(12) United States Patent
Jiang et al.

(10) Patent No.: US 9,429,543 B2
(45) Date of Patent: Aug. 30, 2016

(54) ION MOBILITY ANALYZER, COMBINATION DEVICE THEREOF, AND ION MOBILITY ANALYSIS METHOD

(71) Applicant: SHIMADZU CORPORATION, Kyoto (JP)

(72) Inventors: Gongyu Jiang, Shanghai (CN); Yupeng Cheng, Shanghai (CN); Xiaoqiang Zhang, Shanghai (CN); Wenjian Sun, Shanghai (CN)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/735,876

(22) Filed: Jun. 10, 2015

(65) Prior Publication Data

US 2015/0276676 A1   Oct. 1, 2015

Related U.S. Application Data

(63) Continuation of application No. PCT/CN2013/001508, filed on Dec. 6, 2013.

(30) Foreign Application Priority Data

Dec. 10, 2012   (CN) .......................... 2012 1 0530144

(51) Int. Cl.
*H01J 49/00* (2006.01)
*H01J 49/34* (2006.01)
(Continued)

(52) U.S. Cl.
CPC .......... *G01N 27/622* (2013.01); *G01N 27/624* (2013.01); *H01J 49/004* (2013.01); *H01J 49/22* (2013.01)

(58) Field of Classification Search
USPC .......... 250/281–283, 286.287, 290–293, 526
See application file for complete search history.

(56) References Cited

U.S. PATENT DOCUMENTS 6,791,078 B2   9/2004   Giles et al.
6,812,453 B2   11/2004   Bateman et al.
(Continued)

FOREIGN PATENT DOCUMENTS

CN   101093211 A   12/2007
CN   101728208 A   6/2010
(Continued)

OTHER PUBLICATIONS

Merenbloom, Samuel I. et al., High-Resolution Ion Cyclotron Mobility Spectrometry, Analytical Chemistry, 2009, pp. 1482-1487, vol. 81, No. 4, Bloomington, Indiana.
(Continued)

*Primary Examiner* — Bernard Souw
(74) *Attorney, Agent, or Firm* — Tim Tingkang Xia, Esq.; Locke Lord LLP

(57) ABSTRACT

An ion mobility analyzer, combination device thereof, and ion mobility analysis method. The ion mobility analyzer comprises an electrode system that surrounds the analytical space and a power device that attaches to the electrode system an ion mobility electric potential field that moves along one space axis. During the process of analyzing mobility of ions to be measured, by always placing the ions to be measured in the moving ion mobility electric potential field, and keeping the movement direction of the ion mobility electric potential field consistent with the direction of the electric field on the ions to be measured within the ion mobility electric potential field, theoretically a mobility path of an infinite length can be formed so as to distinguish ions having mobility or ion cross sections that have very small differences.

35 Claims, 15 Drawing Sheets

(51) Int. Cl.
*H01J 49/40* (2006.01)
*G01N 27/62* (2006.01)
*H01J 49/22* (2006.01)

(56) References Cited

U.S. PATENT DOCUMENTS

| | | |
|---|---|---|
| 6,914,241 B2 | 7/2005 | Giles et al. |
| 7,199,362 B2 | 4/2007 | Rockwood et al. |
| 2003/0213903 A1 | 11/2003 | Ichimura et al. |
| 2004/0070349 A1* | 4/2004 | Keady ............... H05H 1/54 315/111.61 |
| 2005/0258449 A1* | 11/2005 | Lutz ............... H01L 31/107 257/186 |
| 2009/0014641 A1 | 1/2009 | Bateman et al. |
| 2010/0193678 A1 | 8/2010 | Clemmer et al. |
| 2011/0121171 A1* | 5/2011 | Clemmer ............ G01N 27/622 250/282 |
| 2011/0291164 A1* | 12/2011 | Bamji ............... G01S 7/4816 257/290 |
| 2012/0004862 A1* | 1/2012 | Hill, Jr. ............. G01N 27/622 702/28 |
| 2012/0091332 A1* | 4/2012 | Makarov ............ H01J 49/40 250/282 |
| 2012/0138785 A1* | 6/2012 | Makarov ............ H01J 49/406 250/282 |
| 2013/0240725 A1* | 9/2013 | Makarov ............ H01J 49/4245 250/283 |
| 2013/0248702 A1* | 9/2013 | Makarov ............ H01J 49/406 250/282 |
| 2015/0040042 A1* | 2/2015 | Huang ............... G06F 3/04817 715/762 |
| 2015/0170898 A1* | 6/2015 | Jiang ............... H01J 49/063 250/282 |
| 2015/0221488 A1* | 8/2015 | Hyeon ............... H01J 49/0009 250/282 |

FOREIGN PATENT DOCUMENTS

| | | |
|---|---|---|
| CN | 102646571 A | 8/2012 |
| GB | 2440970 B | 4/2010 |
| WO | 2010060380 A1 | 6/2010 |
| WO | 2011086430 A1 | 7/2011 |
| WO | 2012029315 A1 | 3/2012 |
| WO | 2012056239 A1 | 5/2012 |
| WO | 2013093513 A1 | 6/2013 |

OTHER PUBLICATIONS

Giles, Kevin et al., Applications of a travelling wave-based radio-frequency-only stacked ring ion guide, Rapid Communications in Mass Spectrometry, 2004, pp. 2401-2414, vol. 18; John Wiley & Sons, Ltd., UK.

Loboda, Alexander, Novel Ion Mobility Setup Combined with Collision Cell and Time-of-Flight Mass Spectrometer, J. Am. Soc. Mass Spectrom, 2006, pp. 691-699, vol. 17, Elsevier Inc.

Laiko, Victor V., Orthogonal Extraction Ion Mobility Spectrometry, J. Am. Soc. Mass Spectrom, 2006, pp. 500-507, vol. 17, Elsevier Inc.

State Intellectual Property Office of the P.R. China (ISR/CN), "International Search Report for PCT/CN2013/001508", China, Mar. 13, 2014.

* cited by examiner

ION MOBILITY ANALYZER, COMBINATION DEVICE THEREOF, AND ION MOBILITY ANALYSIS METHOD

CROSS-REFERENCE TO RELATED APPLICATIONS

This application is a continuation application of International Patent Application No. PCT/CN2013/001508, filed Dec. 6, 2013, which itself claims the priority to Chinese Patent Application No. 201210530144.9, filed Dec. 10, 2012 in the State Intellectual Property Office of P.R. China, which are hereby incorporated herein in their entireties by reference.

FIELD OF THE INVENTION

The present invention relates generally to ion mobility spectrometry, and more particularly to a device for ion analyze that can realize fast separation, accumulation and detection.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Ion mobility spectrometry is a chemical and biological detector that distinguishes and selects ions quickly. In the recent years, the world pays more and more attention on looking for the sensitive detector that is convenient to carry, easy to use and fast to detect in order to protect the continental safety from drug and ordnance smuggling. Due to the high performance of ion mobility spectrometry in such areas, people have developed great interest in researching ion mobility technology and ion mobility spectrometry's performance has been gradually improved these years. Meanwhile, the requirement of applying ion mobility spectrometry in different conditions is becoming more specific and strict. Besides, since the separation mechanism of ion mobility spectrometry is based on the difference of ion mobility in gas phase whose nature is size and shape of ion, ion mobility spectrometry has provided another method of separating that is different from mass spectrometry or chromatography. Traditional practice of ion mobility spectrometry with mass spectrometry or chromatography has improved the performance of individual detector and has lowered the frequency of false positive. Also, ion mobility spectrometry can be used to detect the size of ion so it has great contribute in analyzing the atmosphere aerosol and big biological molecules (like proteomics), It shows great potential in researching and analyzing.

Nowadays, there are two main types of on mobility spectrometry detectors that are put in commercial use: on mobility spectrometer (IMS) and differential mobility spectrometer (DMS). For the first one, the most typical setting is to stack many ring electrodes and isolate them in order to construct the so called drift tube and fill with gas into it up to some certain pressure (usually 1-20 Torr). The stacked ring electrodes have been applied with longitudinal voltage so an axial electric field is formed insider the drift tube. Under the effect of electric field and the collision with neutral molecules, there are directional movements in axial direction besides diffusion. According to ion mobility function:

$$\vec{v} = K\vec{E},$$

where $\vec{v}$ is the drift velocity of ion; K is the ion mobility; $\vec{E}$ is the strength of electric field.

Under the same electric field, due to different mobility of ions, the velocities of ions are different so the time spent in drift tube is different. Different ions are separated based on that. For the second one (DMS), the mechanism of separation of ions is different from the first one. It is not based on the difference of ion mobility but based on the nonlinear change of mobility under electric fields of different strengths. The nonlinear change of mobility is different from ion to ion so DMS can separate ions based on difference of mobility caused by high and low electric fields. Because of simple structure of DMS, the simplest structure of which only consists of two shaft sleeves or two parallel plate electrodes, it is commonly used in developing portable or small devices. Moreover, DMS can work under atmospheric condition without the use of vacuum pump. However, due to the complexity of separation mechanism, its mobility spectrum is hard to take a clear interpretation, there is no extensively recognized way in interpreting such mobility spectrum. Other than two kinds of ion mobility devices previously described, there is another device that is based on separation of mobility is commonly used and called differential mobility analyzer (DMA). The basic structure of DMA is based on the vertical electric filed between two parallel plate electrodes and the drift gas between the plate electrodes in longitudinal direction. Tons enter from the entrance of one plate electrode. When ions enter the drift region between plate electrodes, the overall movement of ions can be divided into two components: movement in the direction of drift gas with the same speed as drift gas and movement in the direction of electric field which is vertical to the direction of ion flow. Based on the ion mobility function, different ions have different speed in the vertical direction so the time ions spent passing the cross-section of drift gas is different which causes the different horizontal distance from entrance when ion reaches opposite plate electrode. However, because of the limitation of the structure of DMA itself and the affection of ion diffusion, the ability of separation of ions is difficult to improve, Usually, tens of resolution or even less its maximum yield so this is not quite an area people are interested in. On the other hand, IMS can reach much higher resolution through longer drift distance or stronger electric field theoretically. Actually, People are trying different methods to improve the performance of IMS.

Alan L. Rockwood and his colleagues from Brigham Young University have demonstrated their patent of cross flow ion mobility spectrometry (U.S. Pat. No. 7,199,362B2) applied in USA. They put drift gas in both radial and axial directions and put electric field in opposite radial direction of drift gas to balance the effect of drift gas. The can make ions with appropriate mobility balanced in the axial direction, hereby realize the correct selection of appropriate ions. Meanwhile, the axial drift gas is transferring ions to next unit or detector. However, the control of drift gas in the axial and radial directions can be tough so the resolution is relatively low. Satoshi Ichimura from Hitachi has mentioned a counter flow ion mobility spectrometry in their patent US20030213903A1 applied in USA. They change the speed of inner drift gas by gradually reducing the inner diameter of drift tube and make the opposite electric filed counteract the effect of drift gas. Thus, different ions with different mobility will stay in different positions across the axial direction and hereby can be separated. However, this method can't constrict the diffusion of ions in radial directions, the huge loss of ions makes detection difficult.

In fact, the idea of using drift gas and opposite electric field to realize the separation/accumulation of ions has been mentioned by J. Zeleny (J. Zeleny, Philos. Mag., 1898, 46, 120-154) in the concept of parallel flow ion mobility spectrometry. This method makes drift gas pass through two parallel grid electrodes and set opposite electric fields between two parallel electrodes, Based on the ion mobility equation, ions with appropriate mobility are captured because their drift velocity is the same as but opposite to that of the drift gas. Other ions are blown off because of inappropriate mobility. Theoretically, this method can separate ions with small mobility differences under relatively low speed of drift gas and weak electric field, Thus, it has good selectivity of ions. However, it is very difficult to introduce ions and also requires very stable drift gas and electric field. Moreover, its characteristics time consuming makes serious ion diffusion that consequently ruins the high sensitivity detection. At last, there is no practical prototype developed. Victor V. Laiko (Victor V. Laiko, J Am Soc Mass Spectrum, 2006, 17, 500-507) has put his effort in theoretical analysis of parallel flow ion mobility spectrometry. He separately developed the formulas of resolution and ion diffusion affected by drift gas and electric fields. Meanwhile, Laiko developed the simulation model to introduce ions into device vertically and then used the numerical analysis method to run simulation test. The result was glad and high resolution was obtained but there is no further experimental result, Obviously, the experiment of this kind must be very difficult to do, Wenjian Sun has announced a device that can be used to separate or accumulate ions in the World Patent WO2010060380. This device has good selectivity of ions by using drift gas and opposite electric fields, meanwhile, accumulating ions.

Alexander Loboda (Alexander Loboda, J Am Soc MassSpectrum 2006, 17, 691-699) from PerkinElmer SCIEX has made a device called counter flow ion mobility device by using segmented quadrupole ion guide and coupled it to an orthogonal injection time of flight (TOF) mass spectrometer. The difference of this ion mobility analyzer from Ichimura's counter flow ion mobility device is that this device does not capture ions at all but uses a counter flow of gas to counteract the force exerted by the electric field. Thus, both of the drift time and the voltage drop over the drift region can be increased. It can not only improve the resolution but also expand the time width of ion peak which extremely elevates the sampling frequency of TOF. This device can reach relatively high resolution in a low atmosphere pressure condition. However, because of the limited length of the drift region, the device's maximum resolution is limited, Although elevating gas pressure can help broaden the retention time of ions and also improve the device's performance, the ion diffusion in the radial direction is out of control. Moreover, the device selects ions by the interaction effect of drift gas and electric fields so the resolving ability of device mainly results from the stability of drift gas and electric fields. In facts, it is very hard to obtain the stable drift gas and electric field.

Kevin Giles (Rapid Common. Mss Spectrum., 2004, 18, 2401-2414) and his colleagues have disclosed a kind of travelling wave ion mobility spectrometry, it causes the difference in strength of local electric field in the drift tube by generating electric pulse in the axial direction in the traditional drift tube ion mobility spectrometry, Ions move forward when the electronic pulses are approaching. Because of different mobility of ions, the distances ions pass through are different. When electronic pulses pass over the ions periodically, the ion groups in axial direction will then be separated due to many times of tiny difference of tiny difference of forward movement. Unlike the traditional on mobility spectrometry, the travelling wave ion mobility spectrometry does not depend on voltage difference between the two ends of drift tube to separate ions but uses local intense electric field in the drift tube to separate ions in a short time again and again so it can realize relatively high resolving power by using relatively low voltage difference. It is considered to be a good ion mobility analyzer and it has been applied on the IMS-MS device of Synapt series provided by Waters Corporation. However, due to the mechanism of separation by travelling wave ion mobility spectrometry and the complexity of separation process, it is hard to get the information about ion mobility or collisional cross section directly from the spectrum.

Other than that, David E. Clemmer (Anal. Chem., 2009, 81, 1482-1497) and his colleagues have disclosed a kind of ion cyclotron mobility spectrometry in which the whole drift tube has eight segments, four bent drift tubes and four ion funnels. The alternative connection of bent drift tubes and ion funnels forms a closed ion cyclotron structure. The ions are urged forward in the drift by the electric field that is generated by a pulse power supply with a certain frequency. When the drift time of ions with certain mobility matches the frequency of the drift electric field, this kind of ions will survive with highest survival percentage in each segment. After experiencing many times of periodic and continuous separation, only ions with appropriate mobility can stay at last. Theoretically, this device can achieve very high ion resolution. However, because of long separation time and ion diffusion in the radial direction, only one kind of ions can survive. The loss of ions is huge which makes sensitivity relatively low. On the other hand, Robert. Harold Bateman has mentioned a kind of ion mobility spectrometry with closed loop structure in the US patent publication No. US20090014641A1. Except for joining the front and rear ends of traditional drift tube together as well as imposing radial confinement field, it is not so special. Particularly, it has adopted an ion path with the pattern of folding loop. Thus, for solving the problem of continuous voltage increment of each segment in the ion drift process, one of segments has to be floated electrically while ions drift in the loop. The work principle by floating the voltage of the segment is similar with that of navigation lock. This may cut away part of the ion cloud and bring uncertain effect on the drift time of ions.

So far, we have demonstrated some developing technologies of ion mobility analyzer. High performance ion mobility analyzer that needs long drift distance requires rapid switching speed of voltage signals to ensure reasonable voltage value of each electrode. On the other hand, the existing ion mobility storage devices that use low electric field needs to balance drift gas and electric field in order to store ions. Unfortunately, drift gas can't be adjusted in a fast, cheap, stable and accurate way like electric field so ion mobility storage device with high resolution is difficult to achieve.

SUMMARY OF THE INVENTION

The invention that will be described in the following context can solve the previously mentioned problems by introducing a dynamic, analytical space. According to the invention, the ion drift length in the ion mobility analyzer can be increased in an arbitrary way. In one embodiment, the ion mobility analyzer comprises the following components:

A plurality of electrodes that surrounds with an analytical space where n ions drift and fly, a first power supply, which applies voltages on the electrodes to create a rotating on mobility electric field (i.e., an ion drift electric field) along a certain space axial in at least part of analytical space. In the analysis process, the ion drift direction is always same with the force direction of the electric field.

In the device, if we select the drift electric field as the reference frame, ions in the drift field will have an extra directional velocity relative to the surrounding background gas. The velocity is always opposite to the direction of the drift electric field if taking the ion mobility analyzer as the reference frame. That is to say, in an experimental environment filled with collisional gas having relatively low speed or essentially static state, in the reference frame of rotating field it can be regarded ions are equivalently encountered with the opposite 'drift gas' which has an opposite movement direction with the rotating field in the reference frame of ion mobility analyzer. Since the velocity and direction of the 'drift gas' are actually decided by the drift field, it is easy to realize the stable adjustment of the velocity of 'drift gas' from zero to ten thousands of meters per second by controlling power supply. Thus, if ions don't leave the ion drift electric field, ions will find an appropriate position in the electric field where they have a same ion drift velocity resulting from the combined effect of the electric field and collisional gas with the velocity of drift electric field so ions with certain mobility can be held for a long time in the ion drift electric field with a finite length and separated from other ions with different ion mobility. Meanwhile, it is different from the travelling wave ion mobility spectrometry because in the analysis process of ion mobility, the ions are not affected by the travelling wave voltage that fast sweeps over the ion drift regions and the wavefront of drift field. Thus, there is no rapid acceleration or deceleration process in the motion and it reduces the influence of clustering and declustering on the result of ion mobility measurement. Hence, the ion mobility achieved with this method is well consistent with the result of tradition drift tube and it makes good comparison of data. Please note the RF voltage for common ion guide transmission is not always necessary in this device, because the ion focusing during the ion mobility drift separation can be achieved by nonlinear field, periodic focusing or applying RF on and off with a duty-cycle.

This is an improvement to this on mobility analyzer, this device of invention can further include a set of confinement electrodes and a mean of power supply to apply voltage on the confinement electrode for confining ions in at least one direction that is approximately perpendicular to the space axis. Usually, in the process of ion drift, except for the movement along the space axis, ions will also have movements perpendicular to the axis caused by diffusion and electric field disturbance. These unexpected movements can get sample ions leave out of analyzer in the drift process. The confinement electrodes and power supply by method can reduce the ion loss.

General ion mobility method relating to balance of drift gas can only work in the linear drift tube. That is because in the curved structure, it is very difficult to keep the drift gas in different regions consistent. However, in this invention, the ion mobility separation axial line can be easily changed to curved axis because the equivalent 'drift gas' is realized by the movements of ion drift electric field without the non-uniformity issue of background drift gas and pressure. It makes it possible to have longer drift distance and improve ion mobility resolving power of the device by folding or twirling the special separation axial line.

Moreover, in an improvement of this invention, a part of the curved axis is joined end to end in order to keep the ion mobility electric field moving circularly in this loop. This approach can further extend the drift distance of ions mobility to improve resolving power of ion mobility.

Furthermore, an additional improvement of this invention is to apply different voltage combinations on the confinement electrodes to split the ion flows. Splitting ion flows has many other benefits besides ion extraction. For example, it can eliminate the difference of drift time of ions locating at inner or outer side of the drift tunnel while making ion trajectory like a '8'-shape topology the effective topologic ring number of which is zero. Besides, it can inject the mobility separated ions into one or more ion analyzer with lower analysis speed for further mass analysis, which can realize a pipe line type of ion mobility-mass spectrometry analysis.

Another application of the invention is to use the ion mobility device that has an enclosed axis as a storage device of ions with specific mobility. In the storage device, by adjusting the moving speed of the moving drift electric field generated by the power supply, it can make the balanced drift speed of at least one ion specie with specific mobility in the device same as the moving speed of the moving drift electric field, which the ions always locate in the device. Thus, a dynamic ion storage device can be formed by using such way.

The ion mobility analyzer in the invention can also be used to accumulate or eject ions with specific mobility in a preset direction. Usually, it can be realized by changes the intensity of the moving drift electric field in the directions of the axis.

The most commonly used way is to use different voltage gradient at different position in the axis. Usually, for the ions with relatively large mobility, they can get balanced with the speed of the drift electric field at the position where the axial voltage gradient is relatively small. On the contrary, for ions with relatively small mobility, they can get balanced with the speed of the drift electric field at the position where the axial voltage gradient is relatively large. Similarly, the different parts of the drift electric field can have different speeds along the axis. Usually it can be realized by deforming the different parts in the axis or dividing the moving drift field into several individual moving drift electric fields each of that has specific voltage gradient. In this situation, ions with different mobility will be held in the different parts having different voltage gradients or speeds and drift at different axial positions with the same speed.

Furthermore, in this invention, the separation process can be improved by taking advantage of this method. The detailed approach is using a non-linear voltage gradient as the moving drift electric field. The intensity of the drift electric field is decreasing in the direction of drift force of ions with specific polarity. Then, ions with different drift velocities will be accumulated at individual balanced positions. The simplest way is decreasing the intensity drift electric field along their individual axis linearly or quadratically. Taking the example of separating positive ions, when the ion species a, b and c responding having mobility relationship $K_1 > K_2 > K_3$ drift in the drift electric field, since the moving direction of the drift electric field is always opposite to the direction of the drag force caused by background gas, the drag force of ion specie c with smallest mobility $K_3$ can get balanced with the electric force firstly, that is $V_c = K_3 E_3$. After that, ion specie c can be accumulated at the average position of movement. On the other hand, ion species a and b with relatively large ion mobility will take more time to get balanced and be accumulated at others two different positions where they drift at the same speed with the drift electric field. Thus, three different ion accumulation regions are formed corresponding to three ion species with different mobility. Notably, even the voltage distribution is not quadratic, only if the voltage gradient of the moving drift electric field decreases along the direction of electric force, the axial focusing effect is till attainable. For instance, ions with large mobility usually experience more time of drift and diffusion to reach their average position. By adopting biquadratic or exponential voltage gradient, ions with different mobility can reach their average points almost at the same time. However, it also makes a more complicated relationship of the average position and mobility.

In the practical analysis process of the invention, except of axial mobility separation, there is also ion diffusion in the direction perpendicular to the axis, which can get the ions out of the analyzer gradually to bring ion loss. In non-uniform axial field, the radial distribution of ions is also affected by the coupled radial field and becomes more divergent, which further depresses the separation result. In the invention, we have several plans for solving the problems.

In one plan, we can superimpose an electric field that has periodic voltage gradient variation along the axis on the moving drift electric field having linear or non-linear voltage gradient. Similar with the way disclosed in the U.S. Pat. No. 6,639,213, in a simplified method the voltage gradient can be formed by applying a voltage distribution to a plurality of electrodes having specific space between one another. Since the axial induced voltage between the adjacent electrodes is lower than that of the electrode nearby, it can accomplish a voltage distribution varying with the pattern basically same with that of the voltage distribution of the electrodes. Meanwhile, based on the periodic voltage gradient in the axial direction, the ions will experience focusing and defocusing periodically, that is so called periodic focusing ion transmission, which can confine ions radially and decrease ion loss.

Moreover, we can superimpose a RF electric field on the moving drift electric filed. The periodical RF electric field can focus and defocus ions at different time. Considering of the transmission characteristics of ions, the RF electric field is formed by applying additional voltage to the confining electrodes with at least one RF power supplies having frequency from 10 Hz to 10 MHz which can realize the periodical focusing ion transmission for most ions.

Furthermore, digital switching technology can also be used to confine ions radially. By switching the output between at least two voltage levels periodically, it can switch the radial focusing state of ions to form periodical focusing ion transmission and generate average pseudopotential to affect the axial voltage gradient. Commonly, the switching frequency is from DC to 10 MHz.

Furthermore, the axial moving drift electric field can also be formed by applying at least two square waveform with different duty cycle to the electrodes to generate average pseudopotential. The average pseudopotenial gradient can be determined by the duty cycle of the voltage applied on the corresponding electrode. Thus, it will not need additional modification or transit high voltage and corresponding power supplies for each of the confining electrodes, as well as will simplify the driver circuit.

As an extension of the invention, the ion mobility analyzer can be combined with mass analyzer of upstream or downstream. Thus, the complex samples like isomers that can't be separated by mass analyzer can be separated by ion mobility analyzer. Besides, the performance of mass analyzers with low or medium resolving power like quadrupole, ion trap etc. can also be improved with the help of ion mobility separation.

Furthermore, since the working pressure of mass analyzer and ion mobility analyzer is different, in order to avoid the influence of gas disturbance on the ion mobility analyzer, an ion guiding device is added between the mass analyzer and ion mobility analyzer. Then, it keeps the region where having large gas pressure variation and gas disturbance away from the ion mobility analyzer and makes it work more stably.

Similarly, for the ion source to produce analyte ions, it can also be designed in such way to avoid its gas pressure affect the ion mobility analyzer. There are two detailed ways, one is using ion sources having similar working pressure with the ion mobility analyzer, like low pressure discharge or ESI sources, glow discharge ion source and cold cathode electron impact source, the other is adding an ion guiding device between the ion source and the ion mobility analyzer to keep the region where having large gas pressure variation and gas disturbance away from the ion mobility analyzer. Both of them can decrease the negative effect on the invention by the disturbance of gas flow and pressure.

One ion analysis method for improving sensitivity can be established by using the ion mobility analyzer in the invention. The detailed analysis process includes injecting at least one ion species with specific mobility into the ion mobility analyzer continuously or discontinuously, accumulating ions at their corresponding positions and ejecting the accumulated ions while they reach a preset position. In such way, the analyte ions can have a better enrichment relative to background noise of electron and chemical ions, which can decrease the detection limit.

One ion analysis method for removing background chemical noise from matrix can be established by using the ion mobility analyzer in the invention. The detailed analysis process includes injecting ions into the ion mobility analyzer, building the moving drift electric field and cutting the parts of the moving drift electric field corresponding to the background noise of electron and chemical ions which can remove the background noise of electron and chemical ions or superimposing radial deflection field or excitement AC field to eject such chemical ions radially.

One ion analysis method for analyzing positive and negative ions simultaneously by using low drift electric field can be established by using the ion mobility analyzer in the invention. The detailed analysis process includes applying voltage gradient with alternative polarity along the moving direction of the moving drift electric field, which makes the positive and negative ions confined in the region of voltage gradient having same or opposite direction with the moving direction of the moving drift electric field, and then separating them base on the relationship of mobility and voltage gradient.

For the ion mobility analyzer of the invention, there are many ion ejection methods among which the most simple one is ejecting ions at the distal end of the axis. Besides, it can also eject ions by applying radial deflection field. For example, after applying an additional high radial deflection field on one portion of the ion confining electrodes, once the separated ions reach the positions of the electrodes, they can be ejected radially with high speed. Its advantage is reducing the ion diffusion and disturbance caused by the edge filed of the electrodes at the distal end of the axis and taking shorter additional drift time while ions leave out.

Besides, the radial deflection field or excitement AC field can be applied on most or all of the ion confining electrodes so that the ions with different mobility distributed at different positions can be detected by a position sensitive detector or a detector array to get a snap shot of the ion mobility spectrum. In addition, a subsequent mass analyzer array can also be used to accept and analyze the ions to get an additional ion mobility-mass spectrum for get more chemical information.

Furthermore, the ion mobility analyzer can also be used as the detector of chromatography devices (gas chromatography, liquid chromatography, ion chromatography and electrophoresis). Comparing with mass analyzer, it requires lower vacuum (usually no less than 0.1 torr), so it does not need expensive turbo molecular pump. Moreover, it has less ion loss due to lower gas pressure difference and good ion separation which is almost orthogonal with optical spectrometry, thermal conduction devices, electron/proton affinity detector. Thus, it has lower detection limit and can provide more chemical information with the combination of other detectors.

Since the ion mobility analyzer of the invention uses the moving drift electric field to analyze ions, the ions will lose balance and get lost by diffusion if stopping moving the drift electric field. For solving this, an additional RF voltage can be applied on the confining electrodes to form multiple local ion traps to confine ions and avoid ion loss by diffusion. At the same time, in the formed ion traps (3D or 2D), it can obtain $MS^n$ information by using mass instable scanning or selective excitement etc. In the normal mobility separation process, it can also be used to accumulate ions with a specific mobility range other than a single mobility.

The ion mobility analyzer of the invention can also be combined with subsequent optical spectrometry. The emitting or exciting light can be injected from the gap between the adjacent confining electrodes or the openings on the confining electrodes. The signal of absorption light or fluorescent light can be detected at the opposite or orthogonal side to get the signal of absorption and emitting light in a specific wavelength range and form the spectrum of the ions with specific mobility. Since the light source can adopt high intensity light source like laser, even single molecule can get pretty large yield of photon, which makes a sample detection result of better sensitivity and selectivity.

In one of the embodiment of the invention, stacked ring structure is used to construct the electrode system of the ion mobility analyzer. The stacked ring structure surrounds an axis. Its ring unit has N pieces of segmented electrodes. The N for every ring unit may be or not be same. The N can be a natural number among 2, 3, 4, 5, 6, or >6.

In one of the embodiment of the invention, parallel long electrodes can be used to form electrode system of the ion mobility analyzer. The ions are distributed along the length of the electrode between the parallel long strip electrodes. The moving direction of the drift electric field is the longitudinal direction of which is perpendicular to the device.

The ion mobility analyzer can also be composed of multiple parallel modules that have the same or similar ion mobility analyzing function. At least one part of electrodes in the parallel units is shared or the whole driving power supply in order to make an array of ion mobility analyzers.

As a simplification or the previous embodiments, at least one part of electrodes is shared in different parallel modules in order to make an array of simple ion mobility analyzers.

As a serial connection possible analyzing method, among ion mobility analyzers composed of individual module or multiple parallel modules, we can apply DC deflection or AC excitation voltages in direction orthogonal to drift electric field moving direction on the electrodes in the space. The ions thereby leave the module unit and transfer to the close parallel units or the ions are ejected from the ion mobility analyzer directly for further mobility analyzing and mass spectrometry analyzing.

The invention has purposed a serial ion mobility analyzing method according to the conditions of the device. The method includes at least two serial low field ion mobility analyzing processes. At least one of them is mobility analyzing process which uses the ion mobility analyzer as separation device of ions with different mobility.

Moreover, the invention has purposed a tandem ion mobility analyzing method with mass spectrometer, to form a two dimensional analysis of IMS and MS. Furthermore, the invention has purposed a serial ion mobility analyzing method whose characteristic is to apply different analyzing conditions on the different parts of ion mobility analyzer or multiple ion mobility analyzing devices. Theses different conditions include at least one of the following: type and distribution of background collision gas, background pressure, temperature and humidity of background gas, the velocity of drift electric field, the change in drift electric field step, radial confinement voltage wave shape and speed of background collision gas. It creates at least two different ion separation or distribution processes according to ion mobility. These two different separation and distribution processes create orthogonal 2D mobility separation so as to improve the selectivity of ion mobility analyzing method.

At last, the invention has purposed the range of working pressure for the ion mobility analyzer. At least one of the following: 1) $10^7$-$10^6$ Pa; 2) $10^6$-$1.5\times10^5$ Pa; 3) $3\times10^5$-$3\times10^4$ Pa; 4) $9\times10^4$-$1\times10^4$ Pa; 5) $1\times10^4$-$1\times10^3$ Pa; 6) $1\times10^3$-$1\times10^2$ Pa; 7)<10 Pa.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment. The drawings do not limit the present invention to the specific embodiments disclosed and described herein. The drawings are not necessarily to scale, emphasis instead being placed upon clearly illustrating the principles of the invention.

EMBODIMENTS OF THE INVENTION

Figure 1:
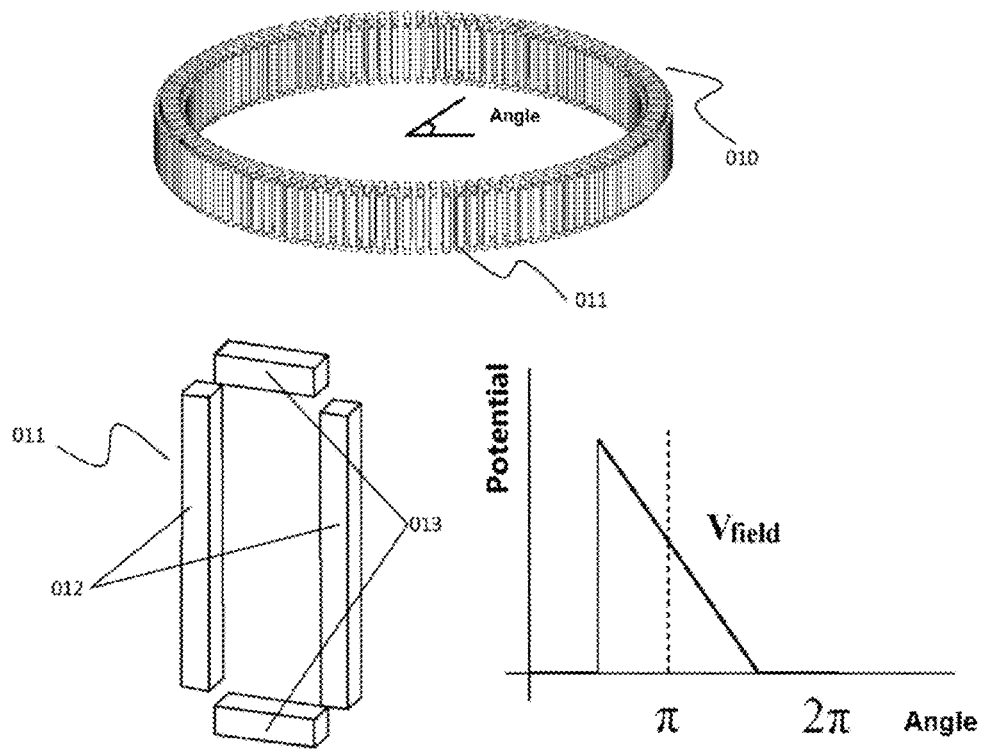
FIG. 1 shows schematically a structure of an ion mobility analyzer and an electrostatic pseudo drift potential distribution in a separation direction according to one embodiment of the invention.

The following description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

As used herein, the terms "comprising," "including," "having," "containing," "involving," and the like are to be understood to be open-ended, i.e., to mean including but not limited to.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to a device for ion analyze that can realize fast separation, accumulation and detection. It can be used in the detection of drugs and explosives or be used in medical analyze. Also, it can be combined with mass spectrometer so as to be used in proteomics, drug metabolism and biopharmaceuticals.

Embodiment 1

As a preferred structure of the ion mobility analyzer 010, the component structure is a closed circular pattern composed of a set of controlled electrode components. Each individual electrode module is composed of a pair of side electrodes 012 and a pair of endcap electrodes 013. The ion mobility analyzer 010 is filled with the gas of certain pressure. The pressure is around 100 Pa-3000 Pa and the gas does not flow in ion mobility analyzer 010. The gas stays static or close to static state. In order to avoid the disturbance of air inlet and outlet to the gas inside analyzer 010, the gas should keep a distance from air inlet and outlet. When it comes to separate ions that enter the ion mobility analyzer, the DC electric potential distribution with linear change is applied on the side electrode 012 corresponding to each individual electrode component unit 011. Also, it needs to rotate in the direction where the angle increases. The rotating speed $V_{field}$ ranges from hundreds of meters to thousands of meters. According to ion mobility equation, $$\vec{v} = K\vec{E},$$

where $\vec{v}$ is the ion mobility velocity; K is ion mobility; E is the strength of the drift electric field.

Figure 2:
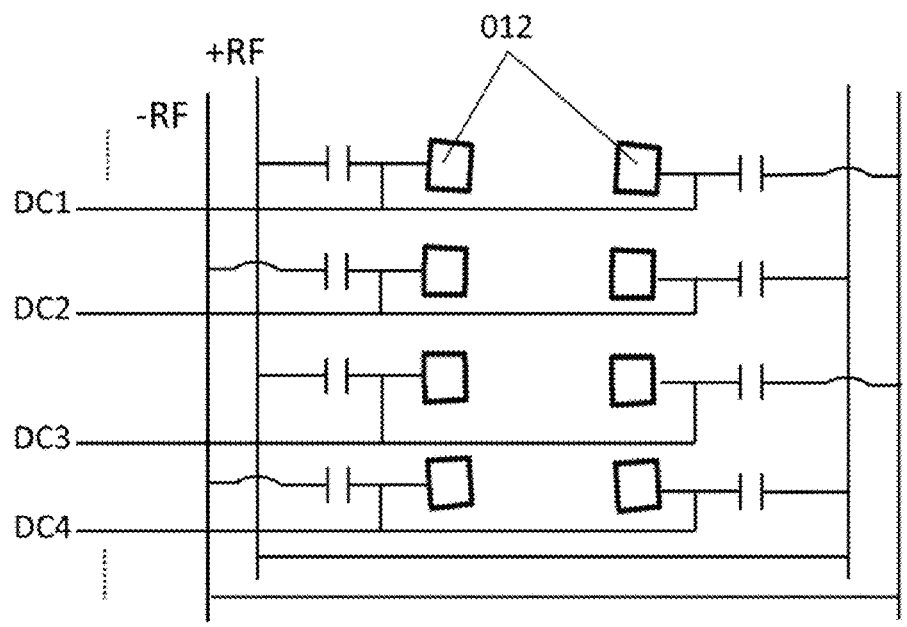
FIG. 2 shows a way to apply voltage on electrodes on each side of the components of the ion mobility analyzer shown in FIG. 1 according to one embodiment of the invention.
Figure 3:
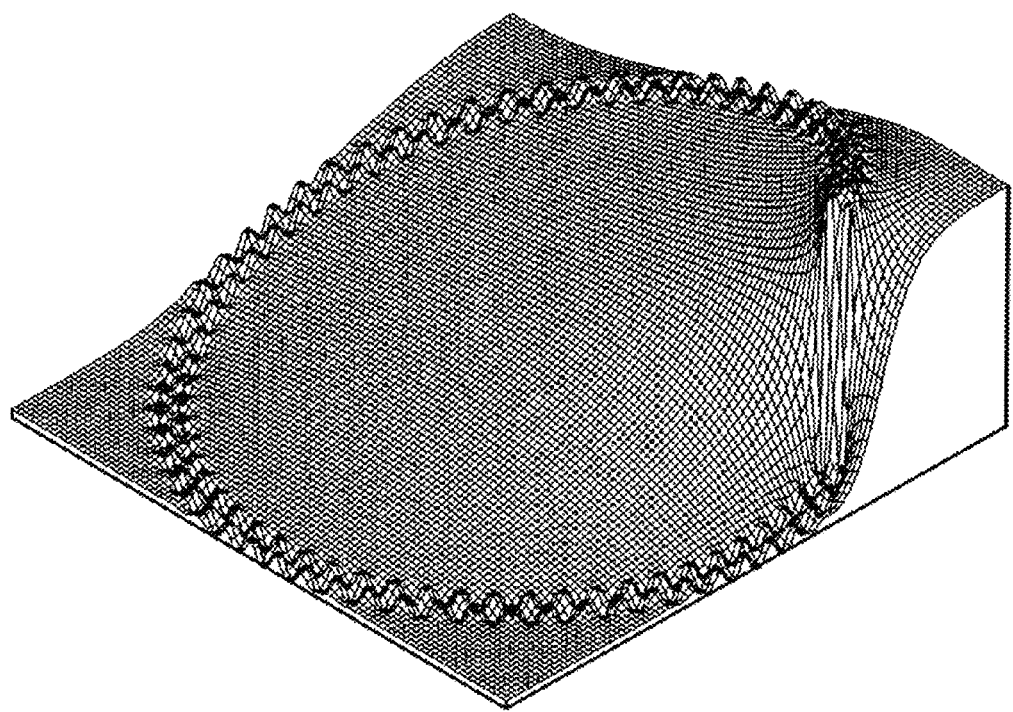
FIG. 3 shows a static electric potential surface diagram that shows the working state of the component of the ion mobility analyzer shown in FIG. 1.
Figure 4:
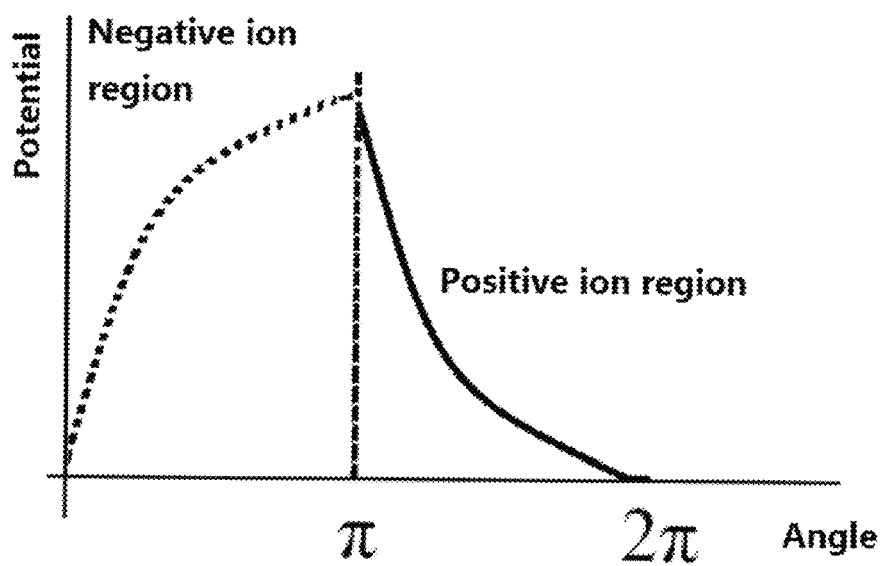
FIG. 4 shows a nonlinear electric potential angular distribution curve that is used to focus ions with different mobility in the space according to one embodiment of the invention.

The rotating speed $V_{field}$ of the DC electric potential distribution should electric match the strength of the electric field so as to make the mobility velocity $v_m$ the same as the rotating speed $V_{field}$ of the electric potential distribution in order to realize the selection of the ions. On the other hand, RF voltage is applied between adjacent side electrodes 011 to constrain the ions for reducing ion loss due to radial diffusion. In this way, the ion transport efficiency is improved. The range of the RF voltage is 20-200 Vpp and the range of frequency is 200 KHz-10 MHz. The way in which each side electrode applies voltage is shown in FIG. 2. FIG. 3 shows the electric surface diagram of DC electric voltage distribution on the side electrode 011 stacked with RF voltage inside ion mobility analyzer 010. From the figure, the DC electric potential distribution forms an electric potential slope in the rotating direction. The mobility velocity of the appropriate ions is the same as the rotating speed $V_{field}$ of the DC electric potential distribution. Finally, the appropriate ions stay on the surface of the slope. Meanwhile, RF voltage creates an alternating radial constraint electric field to counter the radial diffusion of ions so that the ion transport efficiency is improved when analyte ions were trapped or with lower drift speed and the relatively high flexibility is ensured by remove it for higher resolution by prevented the RF heating during the major ion mobility analysis time. Moreover, for further improvement of the duty cycle ratio of the ion transmission, the DC electric potential distribution can have nonlinear change as shown in FIG. 4. Due to the nonlinear change of the electric potential distribution, the various changes happen on the according electric field. Thus, the ions with different mobility are balanced dynamically in electric field of matching strength on the electric potential surface. Ions with different mobility are separated in a constant space distance on the electric potential slope. The resolution in such mode is affected by both strength of electric field and electric step. Also, another advantage of ion mobility analyzer 010 is that it can separate positive and negative ions simultaneously (the electric potential distribution curve of the separated negative ions is shown as the dotted line in FIG. 4). This improves the ion separation efficiency dramatically. Furthermore, the ion mobility analyzer does not need to apply instantaneous DC voltage to sweep through ions like row ion mobility spectrometry. Such drift potential is established on the major part of the ion drift tunnel rotationally so that the analyte ion can be separated inside it, so that the ions can be analyzed with a long time. This helps improve the separation efficiency of the ions and simplify the electric circuits part.

Figure 5:
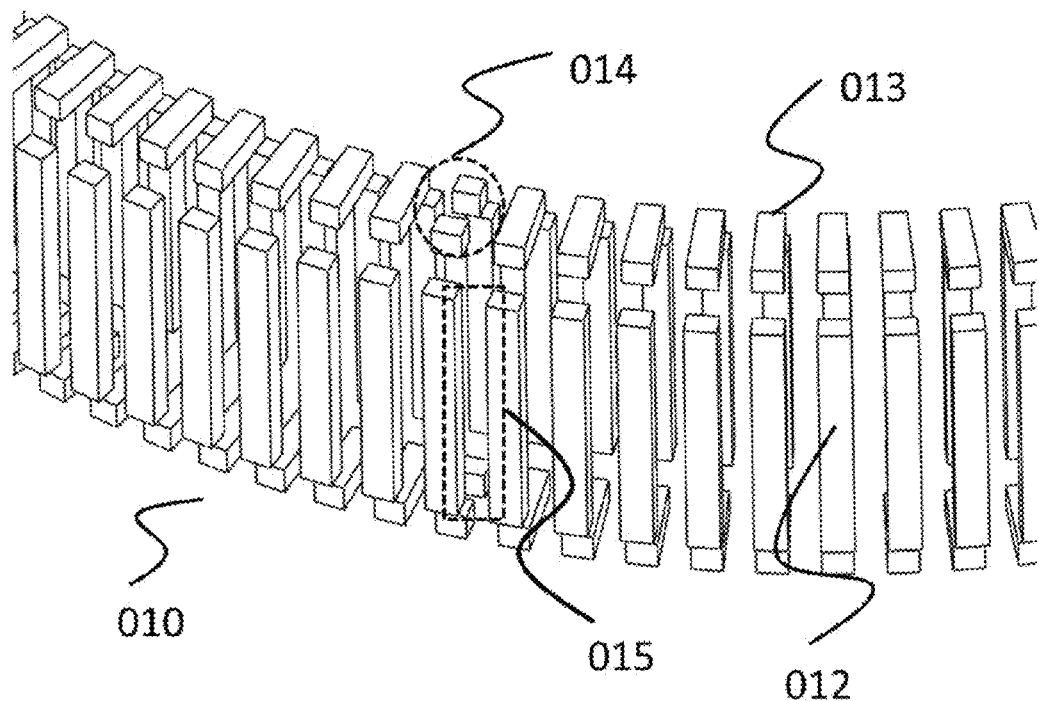
FIG. 5 shows schematically a structure of the electrodes that is used to inject or eject ions according to one embodiment of the invention.
Figure 6:
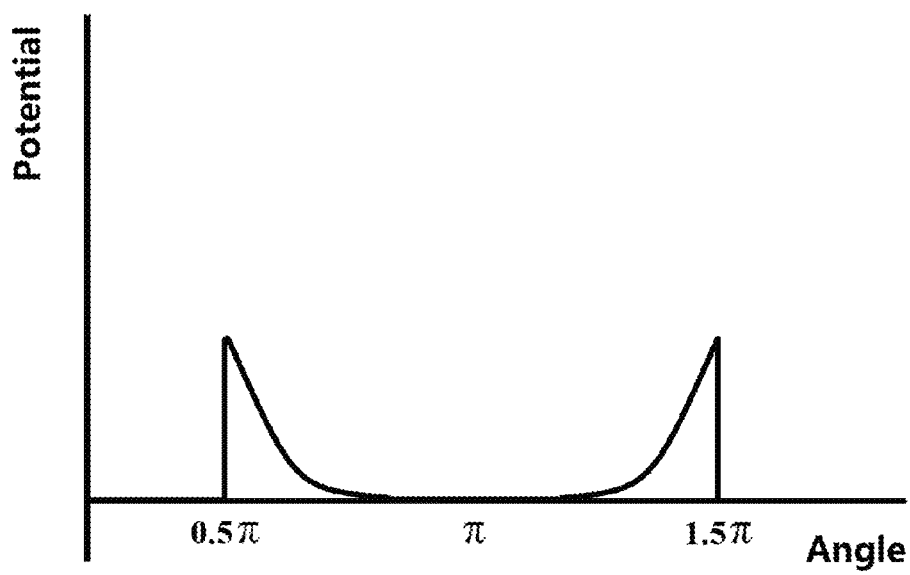
FIG. 6 shows an electric potential distribution curve that is applied to constrain ions in injection or ejection process of ions according to one embodiment of the invention.
Figure 7:
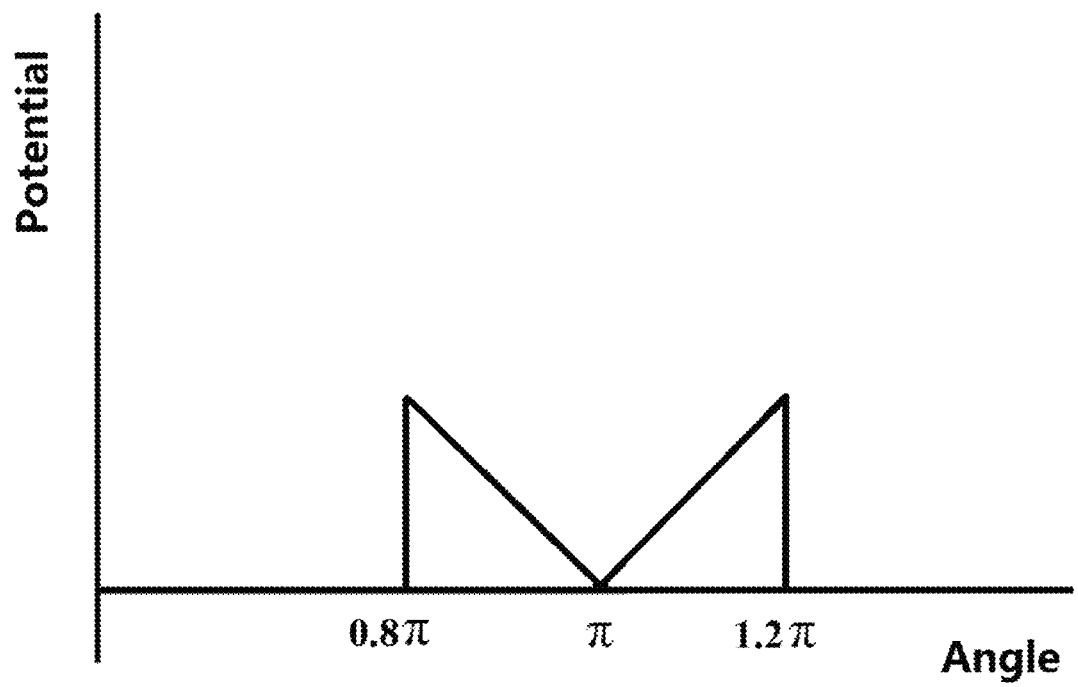
FIG. 7 shows an electric potential distribution curve that is used for further focusing ions in the space according to one embodiment of the invention.
Figure 8:
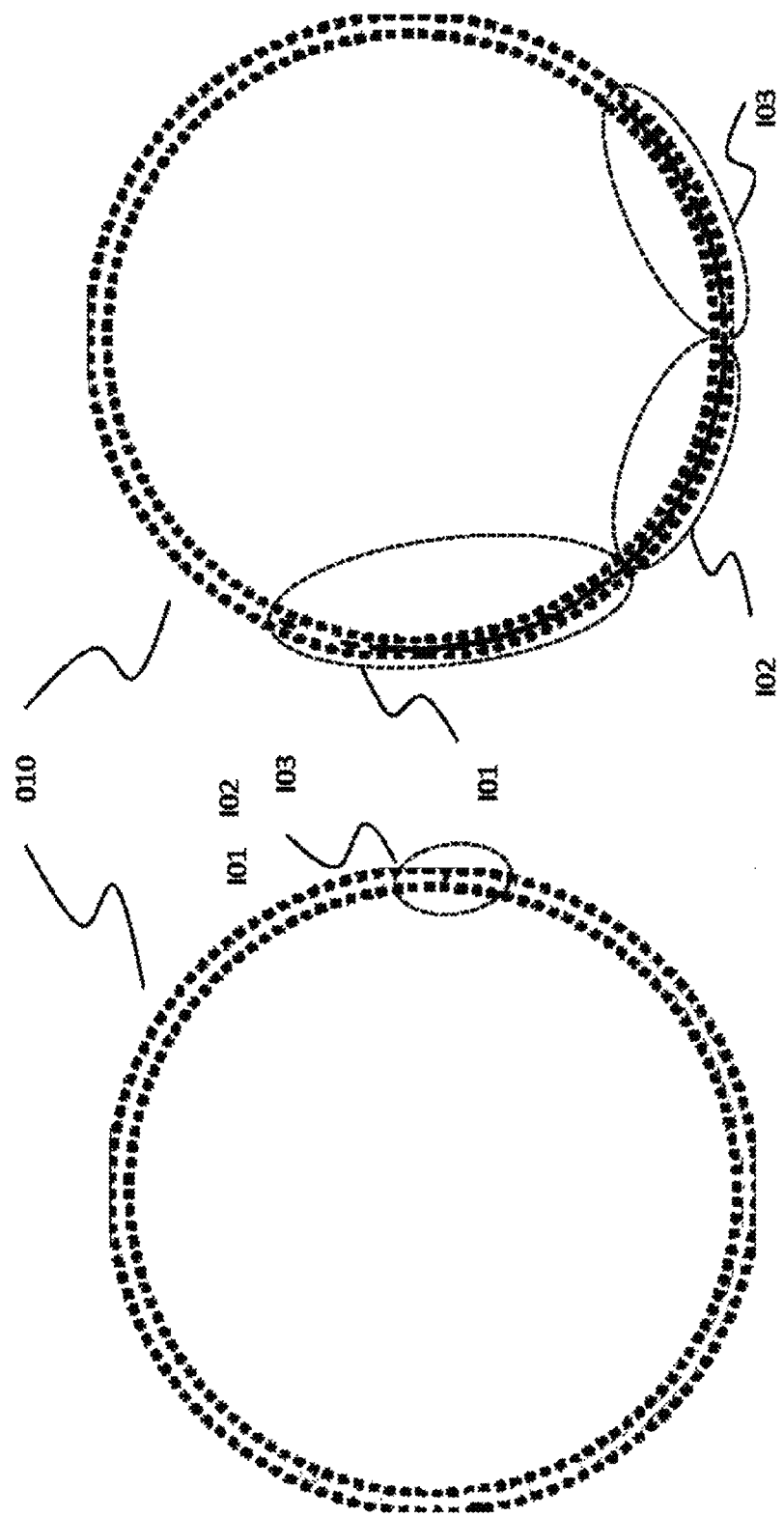
FIG. 8 shows a track of ions with different mobility that explains the effect of separation according to one embodiment of the invention.
Figure 9:
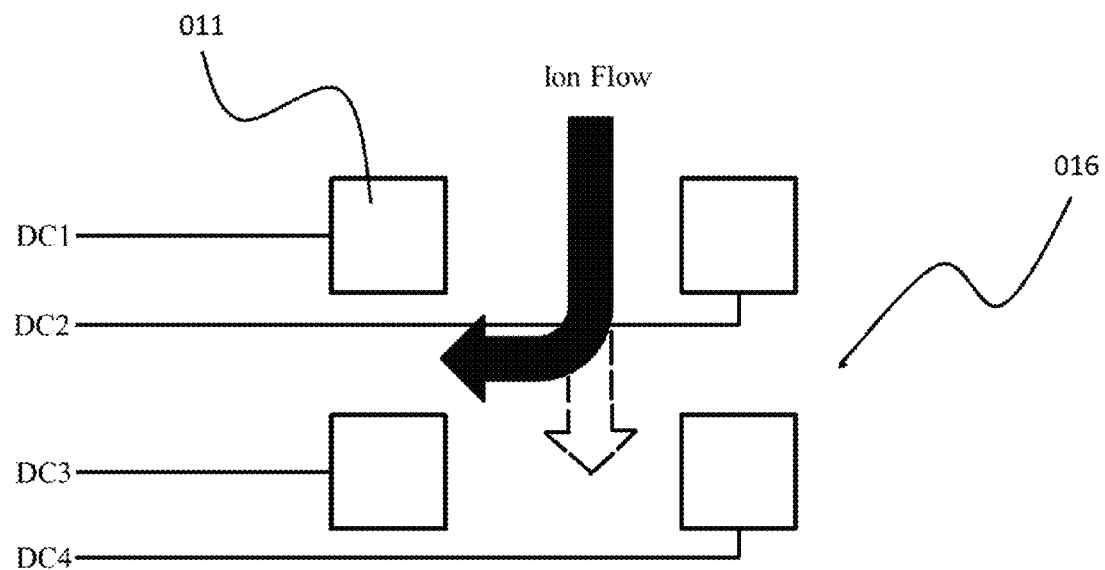
FIG. 9 shows a way in which the voltage applies and the track that the ions pursue when the ions are ejected from the deflection structure according to one embodiment of the invention.

The preferred injection process for ion mobility analyzer 010 is to inject from entry 014 on the endcap 013 as shown in FIG. 5. When the ions start to be injected, the electric potential distribution shown in FIG. 6 ensures the number of ions injected is satisfied and reduce electric charge effect in the space. When the ion injection is completed, in order to ensure the axial starting point of all ions is the same so that the separation time is reduced. An axial compress potention distribution is applied to eliminate the axial distribution of locations when the injection is completed. As shown in FIG. 7, when the accumulation of ion is completed, the axial focusing potential distribution turns into the DC electric potential distribution and starts separation process. FIG. 8 shows the ion tracks of three groups of ions 801, 802 and 803 after initial ion accumulation is competed. When the ions are ejected, it prefers to be ejected from radial outside of the ion mobility analyzer. The exit 015 is located between two adjacent side electrodes 012. When ions are ejected, four side electrodes where the exit 015 is located composes a DC ion deflection device 016 to split the ion flows and lead them out of the ion mobility analyzer 010. At the same time, in order to avoid the ions to stay in the original path (shown as dotted line in the Figure) due to capturing effect of quadrupole field created by RF voltage. The RF voltage on the ion deflection device 016 should be lowered or shut down when the ions are ejected. The other voltages should be applied in the way shown in FIG. 9. Meanwhile, when the ions are ejected, the rotating DC electric potential distribution should be stopped or add a negative DC offset that changes when it sweeps through. That can help ions stay at low electric potential when ions reach the exit of ion ejection.

Figure 10:
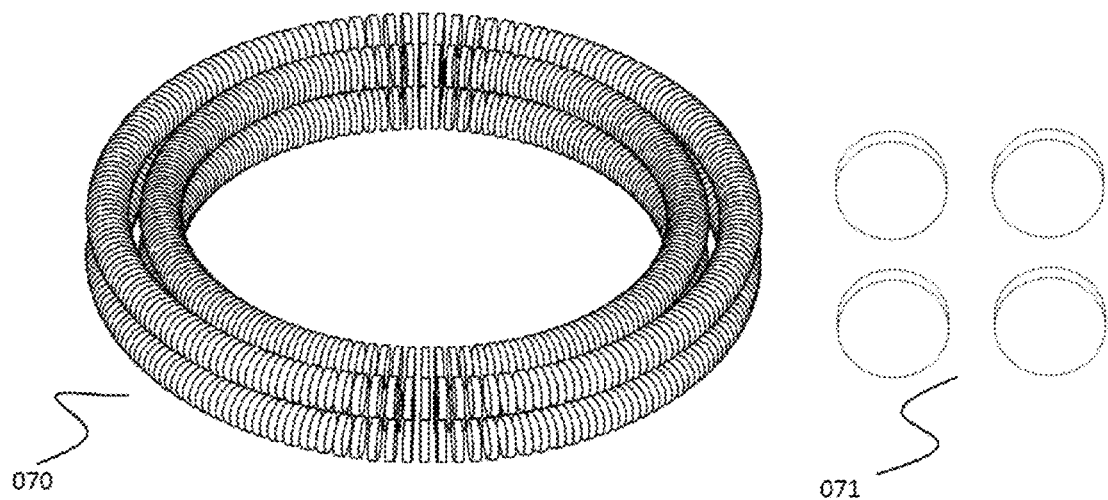
FIG. 10 shows a segmented quadrupole that can be used to substitute the component of the ion mobility analyzer according to one embodiment of the invention.
Figure 11:
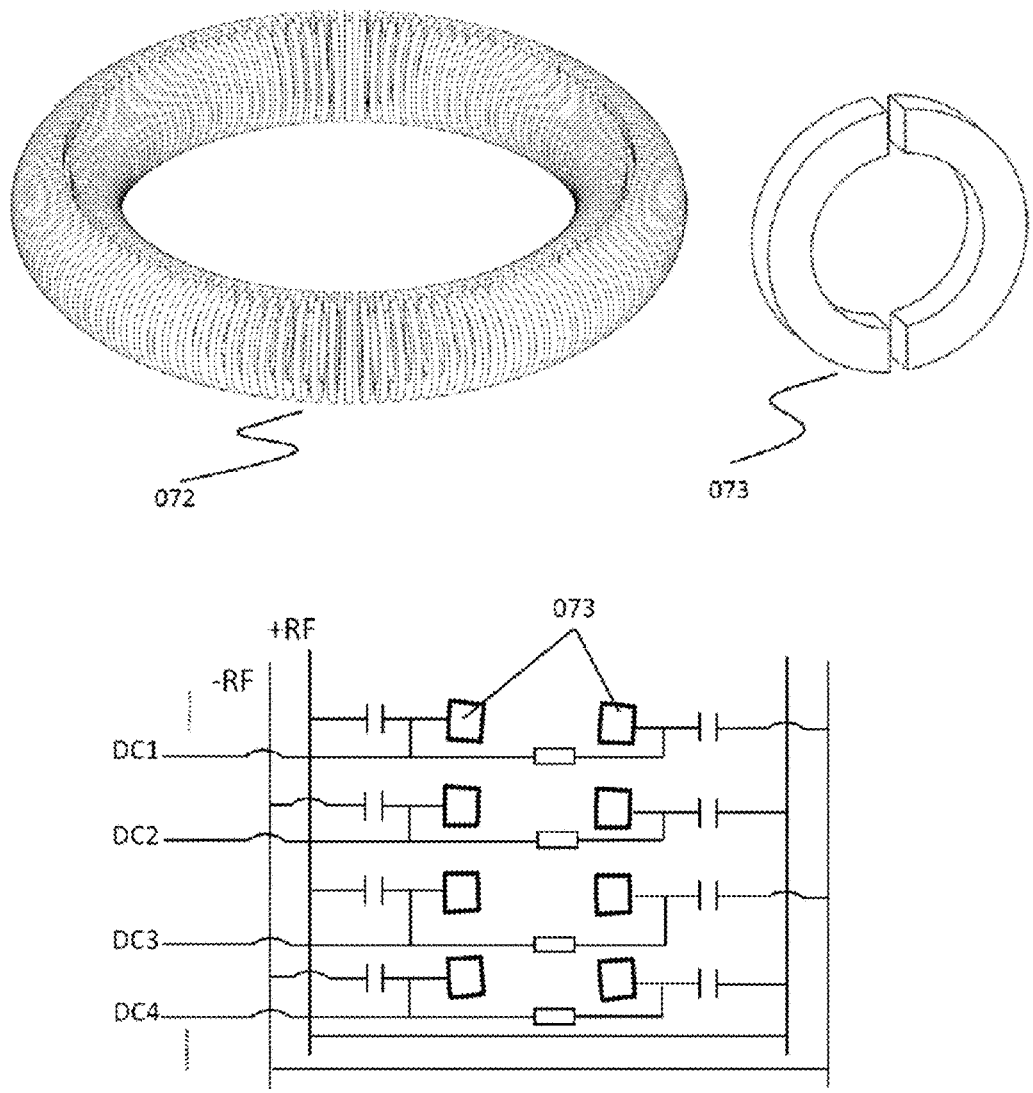
FIG. 11 shows another dipole electrode system ion guide that can be used to substitute the component of the ion mobilizer analyzer according to one embodiment of the invention.
Figure 12:
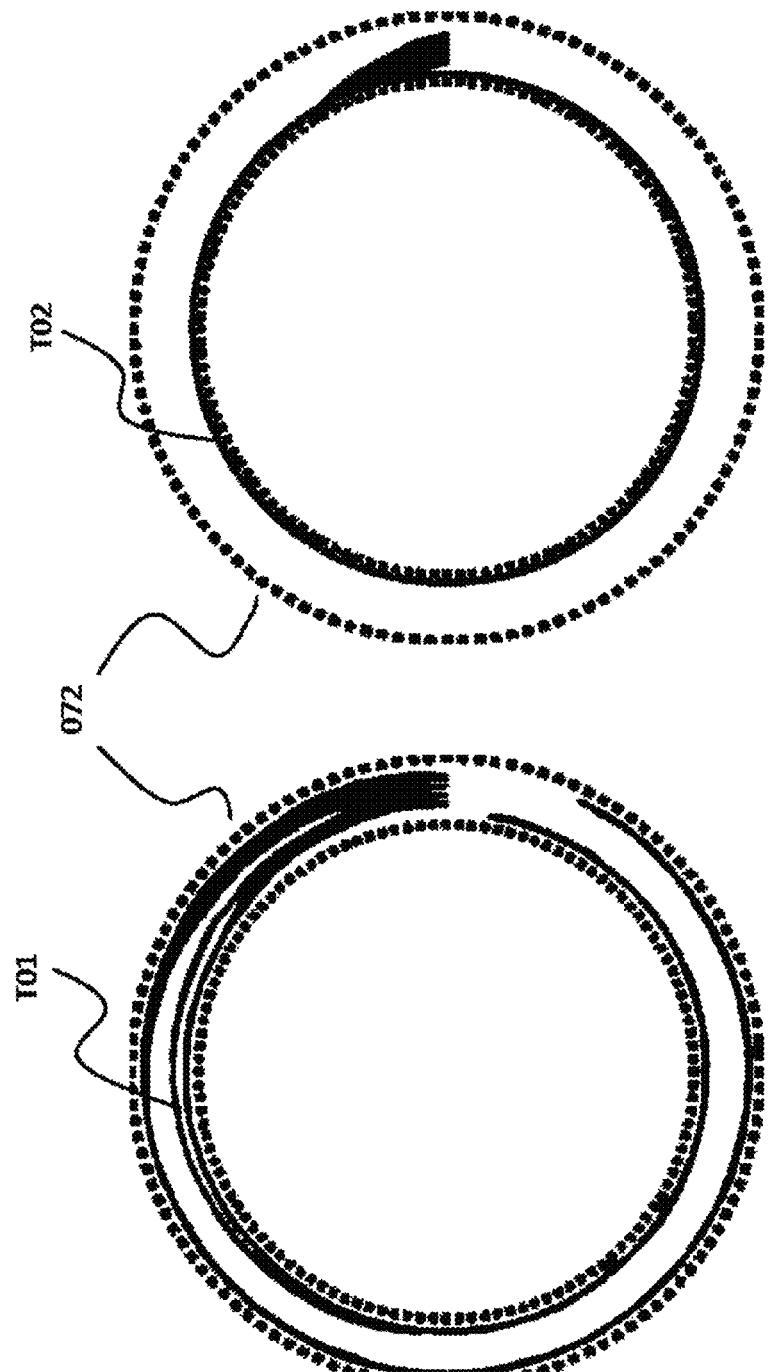
FIG. 12 shows affection of DC offset in the dipole electrode structure to the ion track according to one embodiment of the invention.
Figure 13:
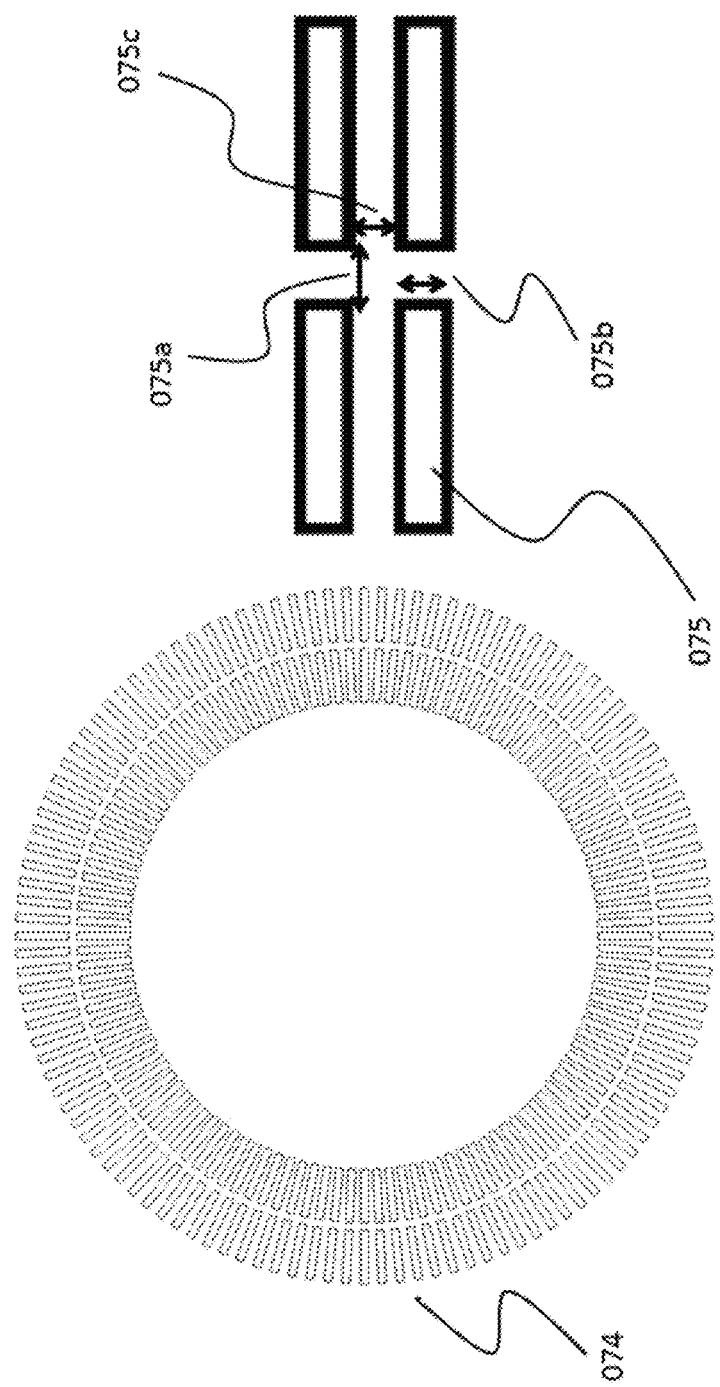
FIG. 13 shows a structure of periodic focusing with the component of the ion mobility analyzer according to one embodiment of the invention.

Moreover, in another practical example of the ion mobility analyzer 010, it can be segmented quadrupole structure 070 as shown in FIG. 10. Each structure unit 071 can be used as traditional quadrupole to constrain ions in radial directions. Also, the electric potential distribution is built between each structure unit 071. The rotating ion drift electric field is formed from scanning the electric potential distribution rotationally. In another practical example we can transform the ion mobility analyzer 010 to the dipole electrodes ion guide structure 072 shown in FIG. 11. The structure unit 073 has larger cross section of ion tunnel so more ions can be held. Except for the RF voltage that needs to be applied on the structure unit 073, dipole potential bias needs to be applied to push the ions to the side of the structure unit 073 in order to ensure the drift tracks of ions are the same. The effect of dipole potential bias on the ions is shown in FIG. 12. From the figure, ion track 1201 split into different ion drift tracks in dipole ion guide thereby ruin the ion resolution completely. When dipole potential bias is applied, the ion track 1202 will accumulate on the same ion track. Also, the periodic ion focusing tunnel structure 074 that does not need RF signals to constrain ions in U.S. Pat. No. 6,639,213 can be another application of the ion mobility analyzer 010. The structure of that is shown in FIG. 13. The periodic ion focusing tunnel 074 is composed of several hole plates or plate electrodes 075. The diameter of the hole 075a, the thickness of the electrode 075b and the distance between electrodes 075c have a ratio of 1:1:1.

Figure 14:
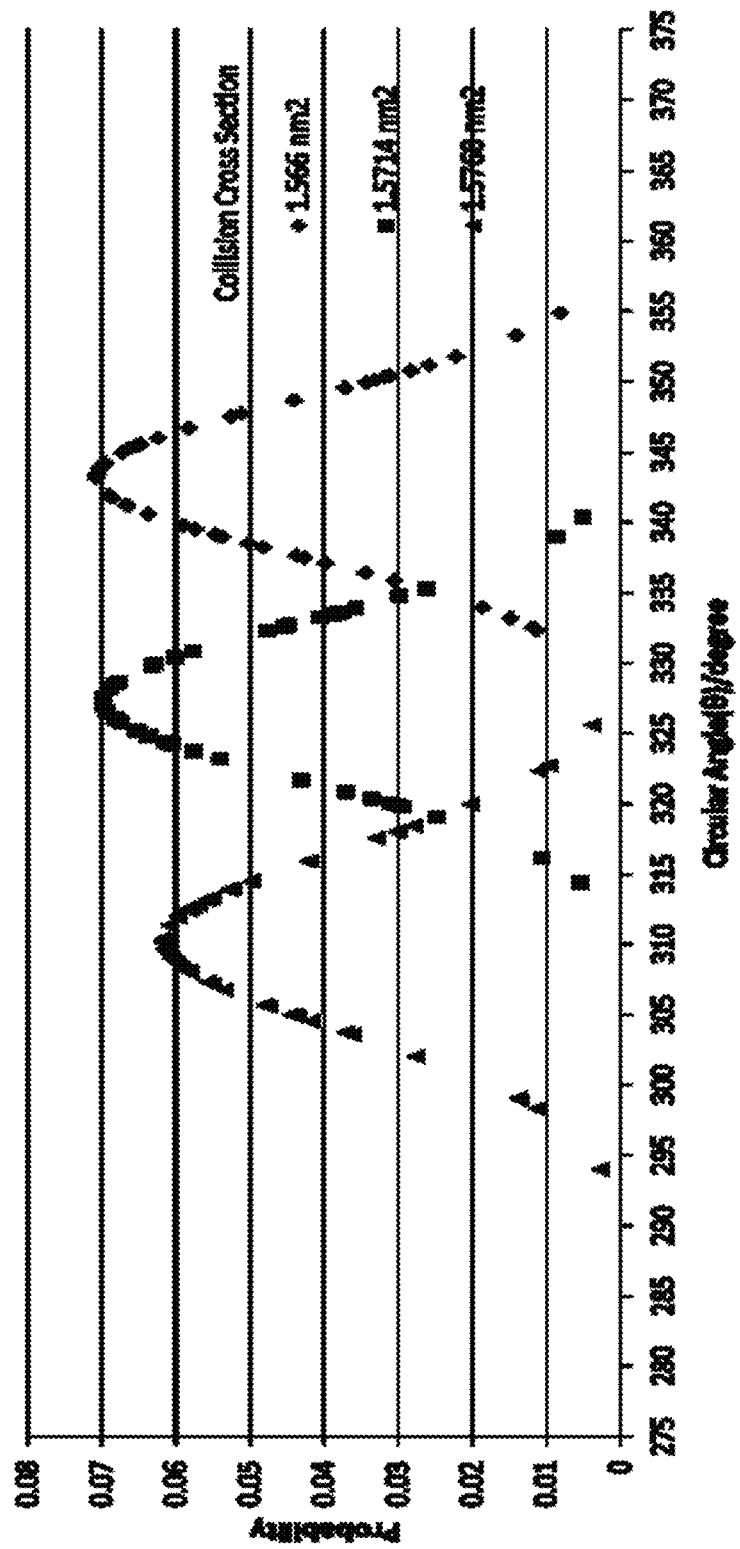
FIG. 14 shows a theoretical simulation diagram of the ion mobility resolution that is obtained using the ion mobility analyzer according to one embodiment of the invention.
Figure 15:
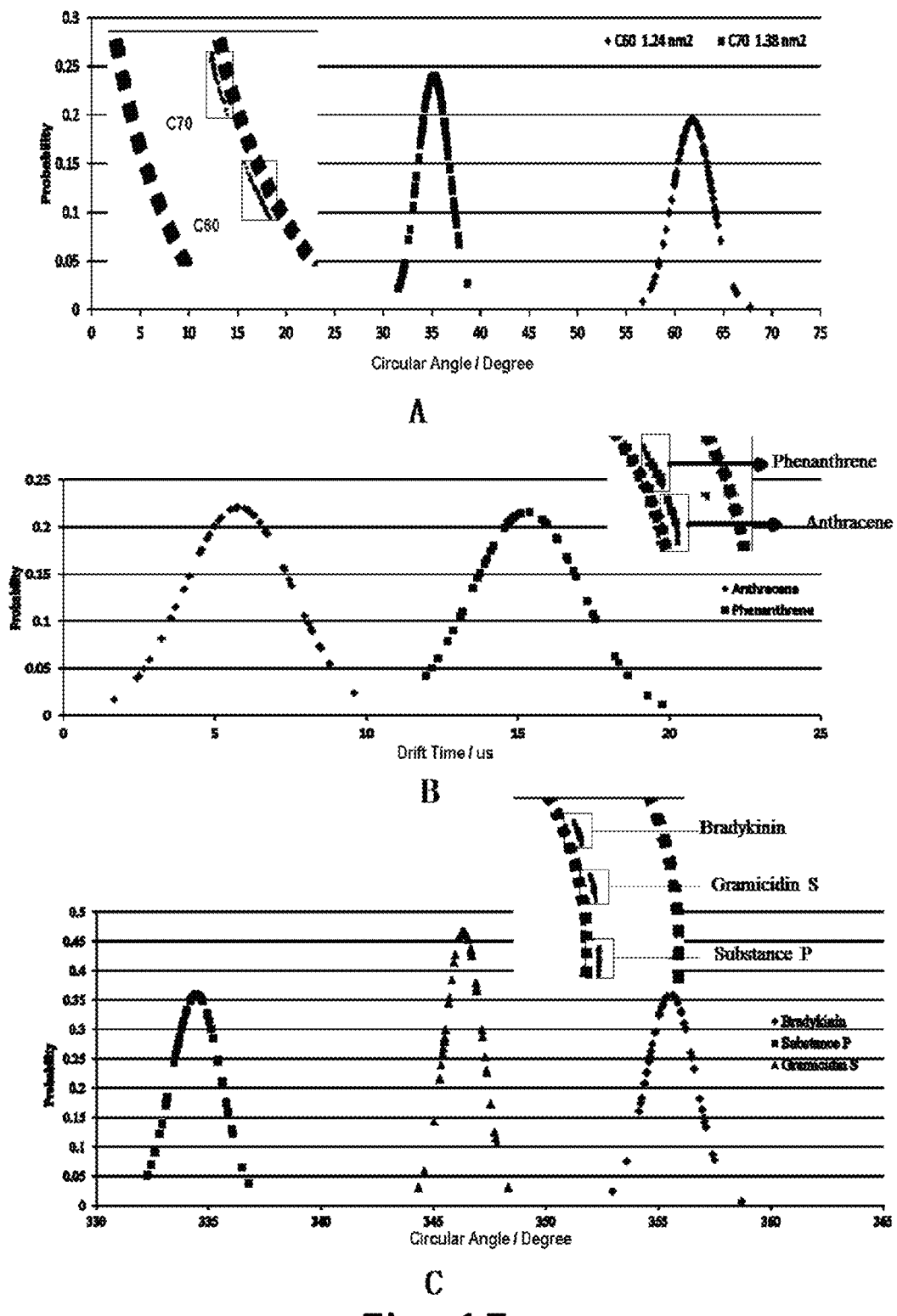
FIG. 15 shows an actual simulation diagram of the ion mobility resolution that is obtained using the ion mobility analyzer according to one embodiment of the invention.

Since the ion mobility analyzer utilizes the opposite interaction of the gas flow and the electric field to select and separate the ions, the gas flow does not actually need to flow at all, the infinite long drift distance can be obtained theoretically and extremely high ion resolution can be achieved. At the same time, the ion drift device can separate different ions simultaneously thereby flexibility is improved. This is an extremely high-efficiency ion drift device. According to simulated experiment, the ion mobility analyzer realize the separation of three different kinds of ions with collisional cross section $\Omega/\Delta\Omega=290$. The separation result is shown in FIG. 14, the higher resolution can be achieved by increasing drift distance or improving electric field distribution. In another simulated experiment, a good separation of fullerene, volatile organic compound and peptide is achieved.

Embodiment 2

Figure 16:
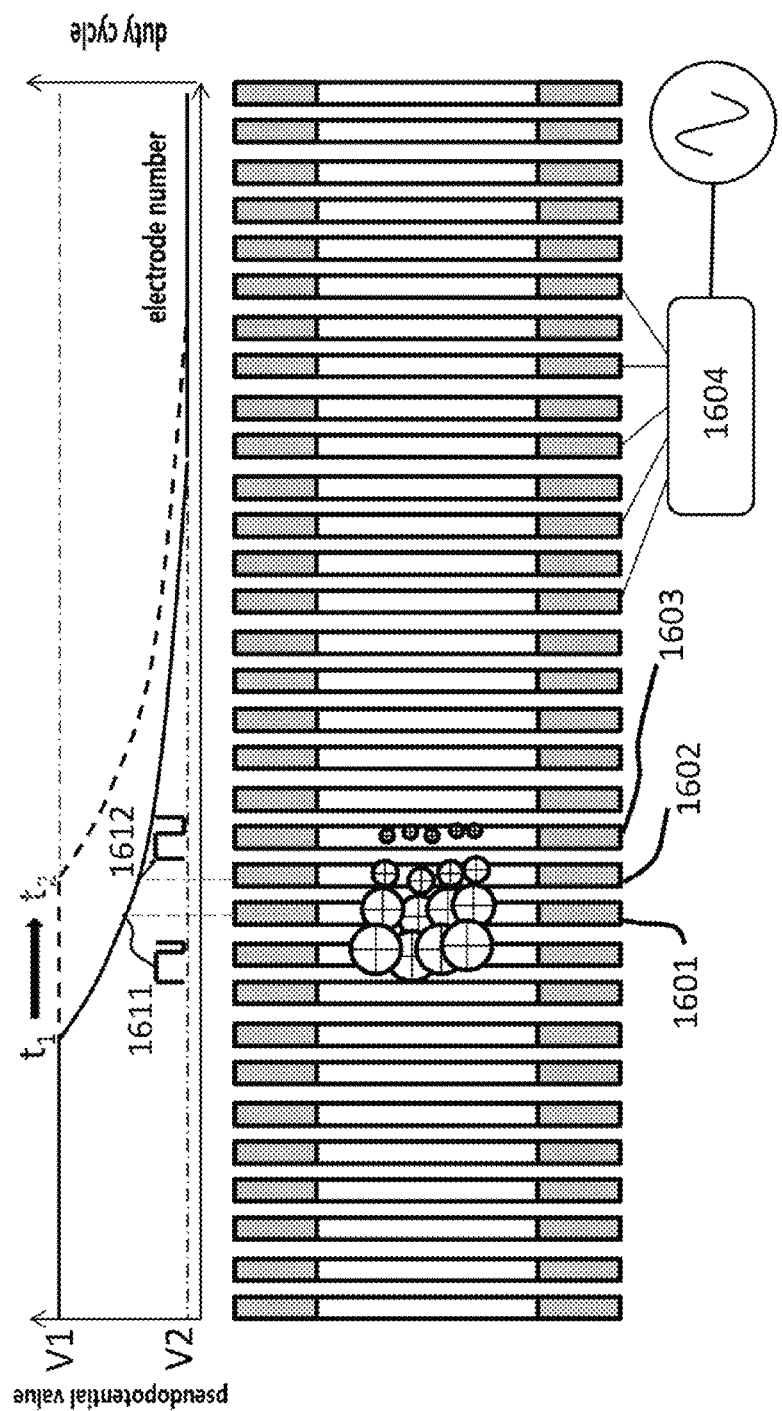
FIG. 16 shows a diagram that shows the principle to form drift potential of the analyzer by alternating the duty cycle of a switched waveform according to one embodiment of the invention.

This example shows another approach to create drift electric field of moving ions. As shown in FIG. 16, in the arrangement of multiple circle electrodes that are parallel to each other, for each electrode, periodic switching waveform was applied between a pair of voltage level with frequency from 10 KHz to 10 MHz, among these, the phase of waveforms applied on adjacent electrodes e.g. 1601 and 1602 are different. Therefore, the trapping fields for ions can be generated. Slightly different from the example 1, in such device the additional drift voltage gradient is not required. It was replaced with the average pseudo-potential voltage value $V_{pseudo}=DV_1+(1-D)V_2$, in which D is the duty cycle ratio of the higher potential voltage V1, and V2 is the lower potential value.

One advantage of the design is the pseudo potential voltage value can be adjusted by the duty cycle, Usually, this way of control can be realized through High Speed Digital Electric Circuit, Digital Signal Processor (DSP), Complicated Programmable Logic Controller (CPLD) or Field programmable gate arrays. For further improvement of the control accuracy. In another method, the precise potential can also be controlled with error comparison feedback loop by analogue or digital circuit. For example, the potential voltage can be processed by voltage divider, differential amplifier, A-D converter in sequence to get the digital difference value of the real potential and a standard value. This value can be used to further control the duty cycle ratio of each electrodes e.g. 1611 or 1612 by digital filtering and comparison, therefore the cost of multi-channel high speed HV power supply can be reduced.

The point is the digital switch can be expanded to more than one pair in the plan so as to introduce other switching waveform potential like V3 into the analyzer on some electrodes. The advantage of the approach is the potential gradient can be adjusted more accurately. When the voltage of V3 is low, for example like low ground potential, the low energy electron flow that lose electrons easily in DC or RF electric field is led into the analyzer during the continuous time segments of the potential V3. Thereby the controllable Electron Capture Dissociation (ECD) is triggered in the analyzer. On the other hand, by using background gas that captures electrons easily like carbon fluorides as the medium of Electron Transfer Dissociation (ETD), ions like the gene segments, larger protein molecules and peptide segments that are hard to be obtained through general approaches can now be dissociated for further analyze that will use serial drift spectrometry or tandem mass spectrometry. Also, the controllable Collision Induction Dissociation (CID) can be processed in the device, the simplest approach to have such process is to add low alternating excitation signal that has different frequency from constraint RF frequency to some electrodes through signal coupling component 1604 by transformer or capacitor. The signal can be single frequency signal. What needs to be pointed out is the excitation can be realized by changing driving wave shape like the duty cycle value of the 1611, 1612 in a short period periodically without introducing any periodical alternating voltage. The simplest approach is to increase M periods (M is an integral number) of cycle with a time value AD, for another M periods the cycle was reduced with the same value AD, the rest cycles still keep the same period time D originally.

In the practical example, we can use other stacked electrode structures as electrode system of the ion mobility analyzer instead of the circular structure. As shown in substitute plan from FIG. 17, the original circular component is composed of N individual segmented electrodes that connect together as a circle. The value of N can be the same or different, the value of N can be natural numbers 2, 3, 4, 5, 6 or bigger than 6. The advantage of the approach is it transfers spatial or timely travelling wave potential well that is necessary for ion constraint to the orthogonal direction of the separation direction. It reduces times the electric field falls or lifts in ion separation direction and it increases the separation ability of ions with different mobility within the same distance.

Similar to that, we can use parallel long electrodes to from the electrode system of the ion mobility analyzer instead of circular structure. The ions distribute between parallel long electrodes along the length of the electrode. The direction of the moving drift electric potential field is the other direction that is also orthogonal to the length of the electrode. The advantage of that is ions are discrete in at least one direction that is orthogonal to separation direction. The mutual repulsion of ions in the ion cloud, which is space charge effect, is reduced but the strength of electric field in separation direction keeps constant in direction that is orthogonal to separation direction. This realizes the ideality of the ion drift process.

Figure 17:
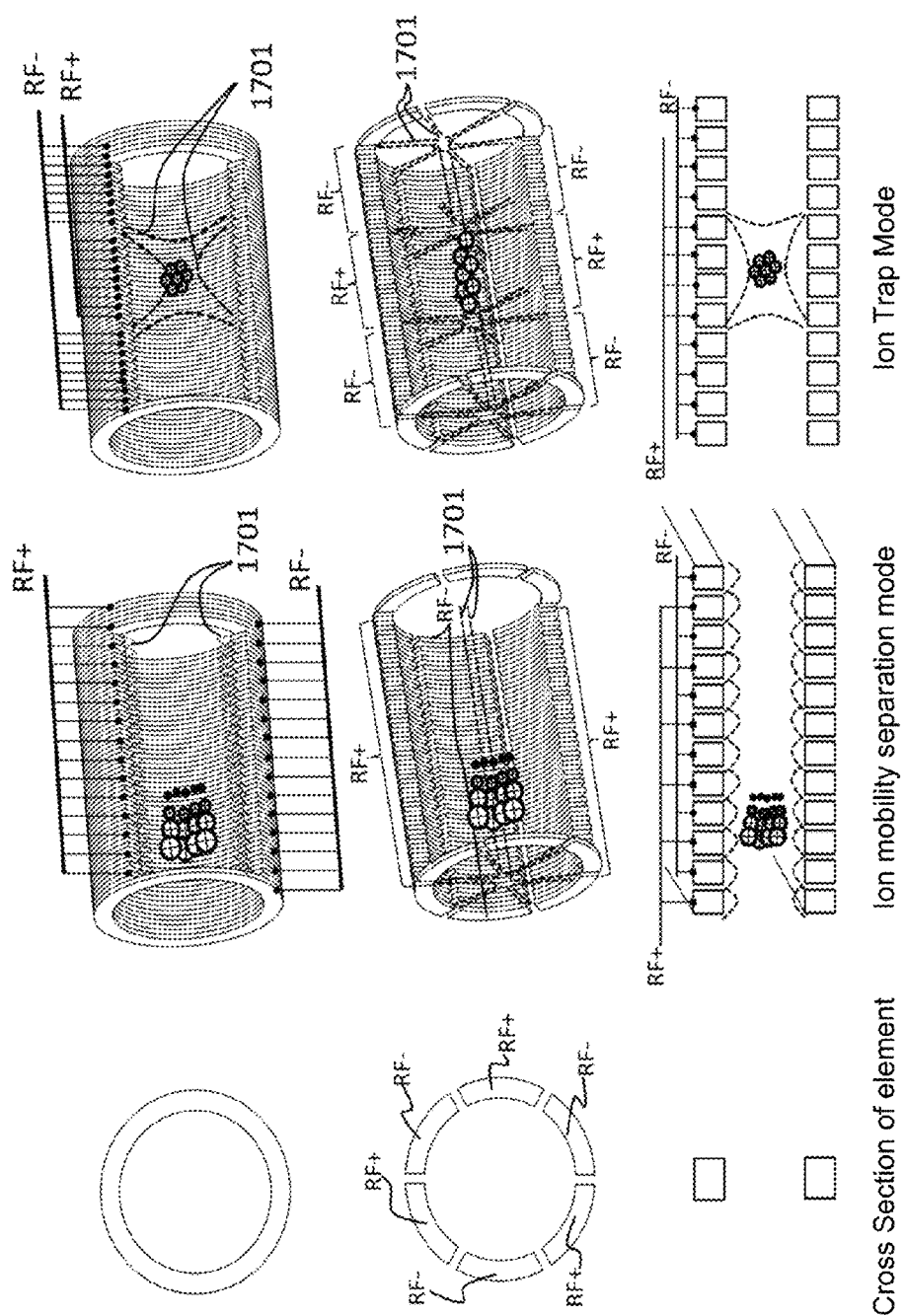
FIG. 17 shows a component of the ion mobility analyzer that is structured from many electrode modules and the switching diagram for working modes of the ion trap in the ion mobility analyzer according to one embodiment of the invention.

As mentioned in the introduction of invention, the previous plans can be used to turn the ion mobility analyzer into single or multiple ion trap arrays. As shown in FIG. 17, in the system of circular electrodes, segmented electrodes and long electrodes, identical or similar RF voltage with enough amplitude can be applied on the single or multiple continuous electrodes in separation direction so that the radius of constraint field will be expanded to the radius of cross section of the drift tunnel. The analyzer will not be ion mobility analyzer anymore. Instead, it turns into a single or multiple ion traps. Certainly, the ion traps or ion trap array with similar structure can also be turned in to the ion mobility analyzer invented in opposite way. If we use traditional sinusoidal RF wave or alternating voltage to realize the transformation of the analyzer's function, it needs milliseconds or even longer time to realize two functional modes due to the limited charging speed of the capacitor. Therefore, some of the ions with different mobility from setting value will be lost by the intermedia unstable field. However, if we use high-speed digital switch to realize the practical example, it only needs sub-microseconds to realize the transformation of two modes (typical time is 1-100 nanoseconds). If we consider that the ions and gas flows move in typical speed, the constraint ions in the device will keep a distance within 0.1 millimeter from the balanced position of the last mode after switching. The ion loss due to mode switching is avoided.

What needs to be pointed out is the structure of power supply is good for constructing an ion mobility analyzer array formed by multiple parallel structure units with the same or similar ion mobility analyzing function. Usually, since the single stacked structure of electrodes has relatively large parasite capacitance (usually >1 nF), it is hard to build small driving electric circuits using sinusoidal wave to constrain voltage, especially for tuning the RF resonance. The driving method of the digital switch can ignore the requirement of the RF resonance Nowadays, the technology of high voltage power supply modules makes the driving of the ion mobility analyzing sets (usually >1 nF) with multiple tunnels possible and convenient. The number of the analyzing sets can be adjusted without affection caused by the change of the resonance point.

Embodiment 3

Figure 18:
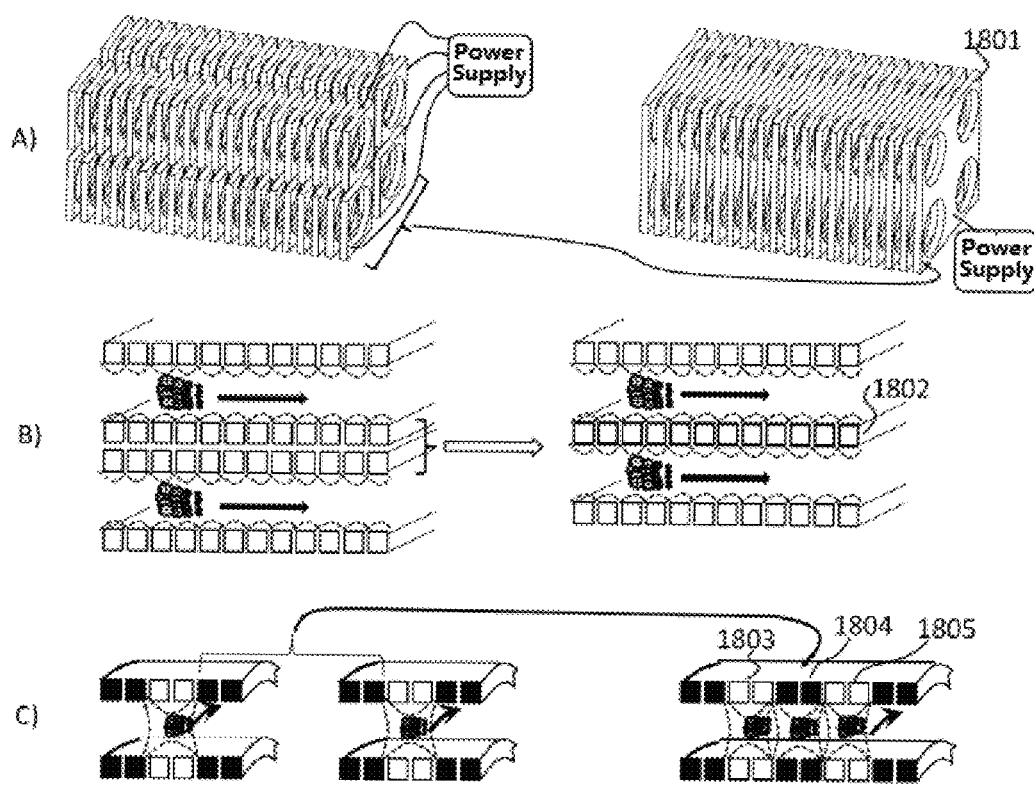
FIG. 18 shows diagrams for array structures of the ion mobility analyzer built by different combinations of the power supply and some working electrodes according to one embodiment of the invention.

As a simplification to the previous embodiments, at least one part of the electrode can be shared among different parallel tunnel structures to form a simple ion mobility analyzer array. This helps simplify the structure of capacitor and devices. FIGS. 18A and 18B show the structure of the ion mobility analyzer array in shared electrodes form constructed by circular and long electrode sets. 1801 and 1802 are two shared electrode parts of the structures. Other than that, as shown in FIG. 18C, the constraint electrodes like 1803, 1804 and 1805 with opposite polarity in different parallel tunnels can be treated as shared constraint electrodes of the adjacent ion mobility analyzer. The each parallel tunnel structure can be separated only by the pseudo potentials. Therefore, the analyte ions can be transmitted between each other tunnels without any hitting-wall loss.

In order to improve the separation effect of the analyzing approach used in the device, in analyzing science, the most typical way is to connect ion mobility analyzing approach with other approaches in series. The simplest practical way is to expel the analyzed ions out from the ion mobility analyzer for further mobility analyze or mass spectrometry analyze. In order to ensure a fast separation process, reduce time spent in transport and inhabit diffusion in transport. The separation process usually happens in the direction orthogonal to the direction of moving drift electric field. The method is to apply DC deflection voltage on the electrode sets near the ions in the orthogonal direction. Also, we can apply alternating resonant excitation voltage in the orthogonal direction as previous practical example so as to make ions leave the structure unit for further mobility analyze or mass spectrometry analyze. The structure of ion mobility analyzer array shown in the example is transferred to the closed parallel structure unit for further mobility analyzes or we can turn another layer of analyzer into quality selective ion trap like previous practical example. The mass spectrometry analyze is realized by using mass scanning or isolation function of the ion trap.

Embodiment 4

Figure 19:
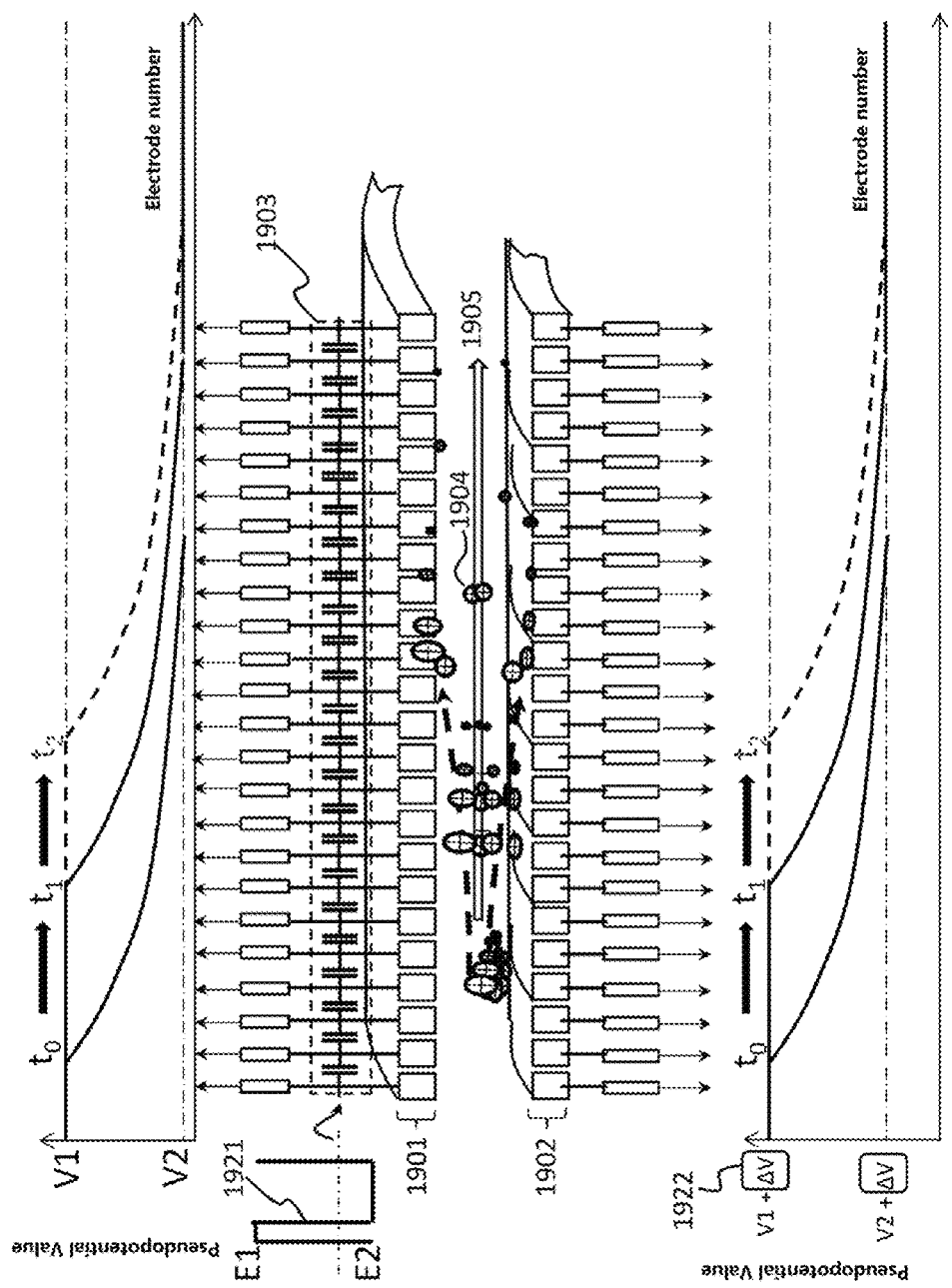
FIG. 19 shows a principal diagram of a two dimensional IMS-differential mobility analyzer according to one embodiment of the invention.

When the analyzing approach is combined with other mobility analyzing approaches, the device can provide typical low field mobility analyzes to at least one analyzing process of two or more low field ion mobility analyzing processes. Then the ions with different mobility are separated. Also, the device can provide a analyzing approach according to the high field differential mobility selection based on low field ion mobility analyze. Taking long electrode shown in FIG. 19 as an example, in the structure unit of the constraint electrodes constructed by a set of long parallel electrode, At least a portion of side electrodes 1901 on the vertical direction of the ion drift direction was applied with a sufficient high amplitude asymmetric AC waveform 1902 by coupling capacitors 1903. (usually the maximum value of the voltage is larger than 1000V or the strength of electric field in the analyzer >3000V/cm), voltage 1922 can be stacked on the electrode set 1902, the voltage can be an alternating voltage having both positive and negative asymmetrical waves or can just be a DC voltage $\Delta V$. The electric field between long electrodes switches constantly in high or low electric filed strength within the positive and negative part of the asymmetrical waveform. Because the polarization or clustering condition for high or low electric field strength are different, so that only under a specified combination of counter voltage and asymmetric waveform amplitude, only a specified mobility alternating characteristic, or ions 1904 with so-called as "differential mobility" value can have a stable trajectory 1905 in the electrodes units. Thus, when different kinds of ions separate in the moving direction of the drift electric field according to ion mobility. The differential mobility value of analyte is also selected so as to achieve 2D separation with higher separation efficiency. Another advantage of the approach is the ions with selected differential mobility value can be self-focused, when circular electrode structure is selected. There is no need to have periodic electric constraint or RF constraint to limit the diffusion of ions in direction orthogonal to moving direction of ion drift field.

What needs to be pointed out is the connected ion mobility analyzing approaches of two dimensions or more dimensions based on the ion mobility analyzer or what happens in the ion mobility analyzer need to keep the diversity of the individual connected analyzing approaches, thus the final separation performance of peaks in multi-dimension of mobility analysis can be maximized. In the device invented, the property of diversity is realized by applying different analyzing conditions in different parts of the ion mobility analyzer or between multiple ion mobility analyzers. These different conditions can be at least one of the following: the components of the background collision gas, background pressure, temperature and humidity of the background gas, the velocity of drift electric potential field, the step change of the electric potential field, the shape of the radial confinement voltage wave and the speed of background collision gas flow. Therefore, there are at least two ion distributions in the space based on different mobility of ions so as to improve the selectivity of ion mobility analyzing approach and realize orthogonal two dimensional or multidimensional mobility separation.

Moreover, because of the features of the technique mentioned in each practical examples and introduction of invention, there are more systems that can be constructed with ion mobility analyzers. One feature of the invention is it can work under different pressures, for instance, high-pressure region ($10^7$-$10^6$ Pa), positive pressure region ($10^6$-$1.5\times10^5$ Pa), normal pressure region ($3\times10^5$-$3\times10^4$ Pa), negative pressure region ($9\times10^4$-$1\times10^4$), low-pressure region of laminar flow ($1\times10^4$-$1\times10^3$ Pa or $1\times10^3$-$1\times10^2$ Pa), transition flow region ($1\times10^2$-10 Pa) and near molecule flow region (<10 Pa). With the assistance of differential mobility selection and transmission, the device can work under pressure $10^7$ Pa or even higher. The lower bound can be around $10^4$ Pa. The higher pressure can obviously prevent the discharge risk for high voltages required by differential mobility selection. Under the circumstances where separation path is needed or ion diffusion problem is severe, the best working pressure range of the device is $3\times10^3$-$1\times10^2$ Pa using periodic DC gradient focusing. For using RF voltage to constrain radial diffusion of ions, the lowest working pressure can be lowered to 3 Pa. Also, the lower working pressure can be obtained by injecting pulsing ultrasound molecular beam along separation direction of ions in the device.

Although the invention is disclosed in previous practical examples but it is not used to limit the probability of the invention. For example, the up flow and down flow of the device can install with continuous ion optical elements like ion introducer, quadrupole mass analyzer and its array, ion funnel, parallel wave ion transportation device, magnetic sector mass analyzer, electrostatic sector energy analyzer and differential mobility analyzer. It can also install with pulse-type ion optical elements like pulse-type ion mobility spectrometer, ion trap and etc. The ion detector of the device can be other pulsing or substantial continuous ion flow mass analyzers like quadrupole, single or multi-turn time of fight analyzer, Fourier transform ion cyclotron resonance (FTICR) or Orbitrap without electron-multiplier tube, or with electron-multiplier or conversion dynode, microtunnel plate or Faraday cup. Also, the ion mobility analyzer not only can be connected with liquid chromatogram or direct analyzing approach but also can be connected with capillary electrophoresis or gas chromatogram. The analyzing ions not only can be generated from ion source in working vacuum condition like electron impact (EI) source, matrix assisted laser deposition ionization (MALDI), but also can be ion source under atmosphere pressure like electrospray ionization (ESI), atmosphere pressure photon ionization (APPI), atmosphere pressure chemical ionization (APCI). The definition of charged ions is not limited to molecular ions, ion clusters and biological molecules used in traditional mobility analyze but can be expanded to mobility analyze of microgram to nanogram level of analyte and select diameter of molecules based on mobility. In conclusion, technologists who work in this field can modify or improve the invention without obeying the spirit and the range of the invention and the protection range of the invention refers to the claims.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An ion mobility analyzer, comprising:
   an electrode system around an analytical space; and
   a first power supply adapted to apply voltages to the electrode system for forming a moving drift electric field in at least a portion of the analytical space along an axis, such that specific analyte ions are always in and have the same moving direction as that of the drift electric field during ion mobility analysis, wherein radio frequency voltages for radial ion confinement are not applied for at least one portion of the analysis time in order to avoid damage on resolution of ion mobility separation through heating by the radio frequency voltages.

2. The ion mobility analyzer according to claim 1, further comprising a group of ion confining electrodes and a second electric power supply for applying voltage(s) to the ion confining electrodes to restrict the ion motion in at least one direction substantially perpendicular to the axis.

3. The ion mobility analyzer according to claim 1, wherein the axis is a curved axis.

4. The ion mobility analyzer according to claim 3, wherein the curved axis includes at least one enclosed part.

5. The ion mobility analyzer according to claim 3, further comprising a third electric power supply for applying different voltages to the ion confining electrodes in order to split the axis of ion trajectories during a specific period of the analysis time.

6. The ion mobility analyzer according to claim 1, wherein the moving speed of the moving drift electric field generated by the first power supply keeps same as the balanced drift speed of at least one specific ion species in the moving drift electric field.

7. The ion mobility analyzer according to claim 2, wherein the moving speed of the moving drift electric field keeps same as the balanced drift speed of at least one specified ion species in the moving drift electric field, wherein the trajectory of the ion species is restricted in the analytical space.

8. The ion mobility analyzer according to claim 1, wherein the strength of the moving drift electric field changes along the axis.

9. The ion mobility analyzer according to claim 8, wherein there are at least two ion species with different mobility drifting at different positions of the axis, wherein the balanced drifting speed of the ion species are the same as the moving speed of the moving drift electric field.

10. The ion mobility analyzer according to claim 9, wherein the gradient of the drift electric field gradually decreases in the drift direction of a specific ion specie with certain polarity.

11. The ion mobility analyzer according to claim 2, wherein the voltage applied to the ion confining electrodes changes periodically along the axis.

12. The ion mobility analyzer according to claim 2, wherein the second power supply generates AC voltage with frequency from 10 Hz to 10 MHz.

13. The ion mobility analyzer according to claim 1, wherein the first power supply is a digital switching power supply switching output between at least two voltage levels and having frequency from 1 to 10 MHz.

14. The ion mobility analyzer according to claim 13, wherein the drift electric field is formed by applying waveforms with at least two different duty cycle ratios switching between high and low voltage level.

15. The ion mobility analyzer according to claim 1 further comprising a upstream and/or downstream ion analyzer of mass-to-charge ratio tandem to the ion mobility analyzer to form an ion mobility—mass spectrometer tandem analytical device for improving the capability of analyzing complex analyte samples.

16. The ion mobility analyzer according to claim 15 further comprising an ion guiding device between the ion mobility analyzer and the ion analyzer of mass-to-charge ratio for keeping the region of different pressure away from the ion mobility analyzer.

17. The ion source for the ion mobility analyzer according to claim 1, which stabilizes the performance of the ion mobility analyzer with at least one of the following methods,
   (a) operated at the similar pressure range as that of the ion mobility analyzer;
   (b) Inserted with an ion guiding device between the ion mobility analyzer and ion analyzer of mass-to-charge ratio to keep the region of different pressure and gas flow turbulence away from the ion mobility analyzer.

18. A method of ion mobility analysis comprising the following operation steps: injecting ions with at least one mobility into the ion mobility analyzer continuously or discontinuously, accumulating said ions with specific mobility at the corresponding positions in the analysis regions for a period of time, ejecting the ions while they arrive at a specified position, and then detecting the ions.

19. A method of ion mobility analysis comprising the following operation steps: injecting ions with at least one mobility into the ion mobility analyzer according to claim 1, removing chemical noises from matrix ions while establishing the drift electric filed in the ion mobility analyzer with at least one of the following methods:

(a) eliminating the matrix ions through destabilizing their axial motion while they move with the moving drift electric field; and (b) ejecting the matrix ions radially by applying additional radial deflection or excitation AC electric field in the rest of the moving drift electric field region.

20. The ion mobility analyzer according to claim 1 for simultaneously analyzing positive and negative ions, wherein a voltage gradient distribution with its polarity varying alternatively is built in the moving drift electric field along its moving direction, which makes the positive and negative ions with specific mobility confined in the regions in which the voltage gradient direction is same with or opposite to the direction of the moving drift electric field, wherein the positive and negative ions are separately analyzed based on ion mobility.

21. A method of extracting analyte ions from the ion mobility analyzer according to claim 1, comprising the following operation steps: applying a high radial deflection field on at least one part of the ion confining electrodes and extracting the mobility separated ions radially with high speed, while they move to the corresponding positions of the said ion confining electrodes.

22. A method of extracting analyte ions from the ion mobility analyzer according to claim 1, comprising the following operation steps: applying a high radial deflection field or AC excitation field on at least one part or all of the ion confining electrodes, extracting the ions of different mobility radially at their corresponding moving position and detecting them or their fragments by a position sensitive detector to form an ion mobility spectrum or tandem ion mobility-mass spectrum, wherein the position sensitive detector is at least one of the following ones:

(a) single position sensitive detector with large area;

(b) an array of ion detectors;

(c) an array of mass analyzers.

23. A chromatography analysis method using the ion mobility analyzer according to claim 1, wherein the ion mobility analyzer is used as the subsequent detector of chromatography analyzer.

24. A mass analysis method using the ion mobility analyzer according to claim 1, wherein the ion mobility analyzer is used as a tandem analyzer of at least a kind of mass analyzers.

25. The ion mobility analyzer according to claim 1, wherein during a different operation time, ion confining RF voltages are applied to at least a portion of ion confining electrodes to form multiple local ion trapping regions for restricting ion diffusion from moving to other regions.

26. An optical spectrometry analysis method using the ion mobility analyzer according to claim 1 comprising injecting the light beam into the ion mobility analyzer and detecting the absorption spectra or fluorescence spectra from the injected ion beam at the opposite or perpendicular position within a specific wavelength window and forming an optical spectra of ions with specific mobilit.

27. The ion mobility analyzer according to claim 1, wherein the ion confining electrodes structure is constructed with stacked electrode units with each being formed with concentric segmented rings, and the number of the segments for each ring can be the same or different, and the number can be 2, 3, 4, 5, 6 or >6.

28. The ion mobility analyzer according to claim 1, wherein the ion confining electrodes are constructed with parallel strip electrode pairs and the planes in which the pairs reside is perpendicular to the axis.

29. An ion mobility analyzer array comprising multiple parallel ion mobility analyzer units each being formed of ion mobility analyzers according to claim 1 and at least a portion of electrodes in the analyzer array share one portion or all of the driving electric power supplies.

30. The ion mobility analyzer array according to claim 29, wherein the parallel ion mobility analyzer units share at least one portion of the ion confining electrodes.

31. A tandem ion analysis method using the ion mobility analyzer according to claim 1 comprising separating ions with one or more mobility spatially in a single or multiple parallel ion mobility analyzer units formed of ion mobility analyzers, applying ejection voltage on the parallel ion mobility analyzer units in a direction substantially perpendicular to the moving direction of the moving electric drifting field, wherein the ejection voltage is DC or AC excitation voltage and transferring the selected ions from the parallel ion mobility analyzer units to adjacent ones or directly ejecting out the ions.

32. A tandem ion mobility analysis method using the ion mobility analyzer according to claim 1, wherein in at least one of two adjacent ion mobility separation processes, the ion mobility analyzer is used as a ion mobility separation device.

33. A tandem ion mobility analysis method using the ion mobility analyzer according to claim 1, wherein at least one asymmetric dual polarity high voltage AC waveform is applied on one portion of the ion confining electrodes to form a differential mobility separation field in the direction perpendicularly to the moving direction of the moving drift electric field, which selects ions with specific differential mobility while separating ions by mobility in the moving direction of the moving drift electric filed.

34. The tandem mobility analysis method according to claim 33, wherein applying two or more different mobility analysis conditions in different portions of the mobility analyzer or among different mobility analyzers; these conditions including composition of background collision gas, pressure of gas, temperature of gas, humidity of gas, moving speed of drifting electric field, the gradient of drifting electric field, the radial confining voltage waveform and/or the flow rate of background gas, or a combination of the above in order to form at least two different ion spatial distributions.

35. The ion mobility analyzer according to claim 1, wherein the operating pressure of the ion mobility analyzer is within at least one of the following pressure range 1) $10^7$-$10^6$ Pa, 2) $10^6$-$1.5\times10^5$ Pa, 3) $3\times10^5$-$3\times10^4$ Pa, 4) $9\times10^4$-$1\times10^4$ Pa, 5) $1\times10^4$-$1\times10^3$ Pa, 6) $1\times10^3$-$1\times10^2$ Pa, 7) $1\times10^2$-10 Pa and 8) <10 Pa.

* * * * *